United States Patent [19]

Raymond et al.

[11] Patent Number: 5,624,901

[45] Date of Patent: Apr. 29, 1997

[54] 3-HYDROXY-2(1H)-PYRIDINONE CHELATING AGENTS

[75] Inventors: Kenneth N. Raymond; Jide Xu, both of Berkeley, Calif.

[73] Assignee: The Regents of the University of California, Oakland, Calif.

[21] Appl. No.: 285,640

[22] Filed: Aug. 2, 1994

Related U.S. Application Data

[63] Continuation-in-part of Ser. No. 227,969, Apr. 15, 1994, abandoned.

[51] Int. Cl.$^6$ .................... A61K 38/06; A61K 38/08; A61K 31/44; C07D 401/12
[52] U.S. Cl. ............... 514/17; 514/18; 514/348; 514/350; 546/256; 546/261; 546/268.1; 546/296; 530/329; 530/330; 530/331
[58] Field of Search .................. 546/6, 296, 256, 546/261, 268.1; 514/188, 348, 350, 17, 18; 530/329, 330, 331

[56] References Cited

U.S. PATENT DOCUMENTS 4,698,431  10/1987  Raymond et al. .................. 546/298

OTHER PUBLICATIONS

White et al., Journal of Medicinal Chemistry, vol. 31 (No. 1), pp. 11–18, Jan. 1988.

Scott et al., Journal of the American Chemical Society, vol. 107 (No. 13) PP. 6540–6546 Nov. 1985.

Xu et al., "Specific Sequestering Agents for the Actinides. 28. Synthesis and Initial Evaluation of Multidentate 4-Carbamoyl-3-hydroxy-1-methyl-2-(1H)-pyridinone Ligands for in Vivo Plutonium (IV) Chelation[1,]" J. Med. Chem. 1995, 38, pp. 2606–2614.

P. Durbin et al, "In vivo Chelation of Am(III), Pu(IV), Np(V) and U(VI) in Mice by TREN-(Me-3,2-HOPO)", Chemical Abstracts, vol. 122, No. 1, 2 Jan. 1995, p. 517.

Uhlir et al., "Specific Agents for the Actinides. 21. Synthesis and Initial Biological Testing of Octadentate Mixed Catecholate-Hydroxypridinoate Ligands", J. Med. Chem. 1993, 36, pp. 504–509.

R.J. Bergeron et al., "Catecholamide Chelators for Actinide Enviromental and Human Decontamination", Chemical Abstracts, vol. 105, No. 25, 22 Dec. 1986, Columbus, Ohio, US, Abstract No. 221872Z, p. 374.

P.W. Durbin et al., "Specific Sequestering agents for the Actinides: Enhancement of Puutonium–238 Elimination from the Emice by Poly(catechoylamide) Ligands", Chemical Abstracts, vol. 101, No. 15, 8 Oct. 1984, Columbus Ohio, US; Abstract No. 125980e, p. 328.

R.A. Bulman et al., "An Examination of Some Complexing Agents for Ability to Remove Intracellularly Deposited Plutonium", Chemical Abstracts, vo. 92 No. 13, 31 Mar. 1980, Columbus, OH, US: Abstracts No. 106582f, p. 286.

M. Streater et al., "Novel 3-hydroxy-2(1H)-pyridinones. Synthesis, Iron(III)-Chelating Properties, and Biological Activity", Journal of Medicinal Chemistry, 1990, vol. 33, pp. 1749–1755.

*Primary Examiner*—Alan L. Rotman
*Attorney, Agent, or Firm*—Townsend and Townsend and Crew LLP

[57] ABSTRACT

Disclosed is a series of improved metal chelating agents, which are highly effective upon both injection and oral administration; several of the most effective are of low toxicity. These chelating agents incorporate within their structure 1-hydroxy-2-pyridinone (1,2-HOPO) and 3-hydroxy-2-pyridinone (3,2-HOPO) moieties with a substituted carbamoyl group ortho to the hydroxy or oxo groups of the hydroxypyridinone ring. The electron-withdrawing carbamoyl group increases the acidity of the hydroxypyridinones. In the metal complexes of said chelating agents, the amide protons form very strong hydrogen bonds with its adjacent HOPO oxygen donor, making these complexes very stable at physiological conditions. The terminal N-substituents provides a certain degree of lipophilicity to said 3,2-HOPO, increasing oral activity. Also disclosed is a method of making the chelating agents and a method of producing a known compound, 3-hydroxy-1-alkyl-2(1H) pyridinone, used as a precursor to the chelating agent, safely and in large quantities.

43 Claims, 2 Drawing Sheets

3-HYDROXY-2(1H)-PYRIDINONE CHELATING AGENTS

The Government has rights in this invention pursuant to Contract No. DE-AC03-76SF00098 awarded by the U.S. Department of Energy. The uranium and plutonium chemistry is supported through DOE. The iron chemistry is supported on the Berkeley campus by NIH grants AI 11744 and DK 32999. The plutonium decorporation and ligand toxicology are supported by NIEHS grant ES 02698.

CROSS-REFERENCE

This application is a continuation-in-part of an earlier filed application entitled "1,4-Disubstituted 3-Hydroxy-2 (1H)-Pyridinone Chelating Agents," Ser. No. 08/227,969, filed Apr. 15, 1994, now abandoned.

BACKGROUND OF THE INVENTION

1. Field of the Invention

The present invention relates generally to improved therapeutic metal chelating agents which are highly effective and have low toxicity upon injected and oral administration, and in particular to chelating agents which incorporate within their structures 1-hydroxy-2-pyridinone (1,2-HOPO) and 3-hydroxy-2-pyridinone (3,2-HOPO) moieties with a carbamoyl group substituted on the ring carbon atom ortho to the hydroxy or oxo group of the HOPO ring.

2. Description of Related Art Including Information Disclosed UNDER §§ 1.97–1.99

Siderophores are highly selective and effective ferric chelating agents synthesized and released by microorganisms to ensure the presence of sufficient iron in solubilized form for cell reproduction. It was recognized early on that the affinity and selectivity of the siderophores for ferric ion made these compounds good candidates for therapeutic iron removal agents. This is particularly true for patients who suffer from blood diseases such as beta thalassemia, the treatment of which requires the regular transfusion of whole blood and results in the accumulation of massive tissue iron deposits. Because of the similarity in coordination properties between Fe(III) and tetravalent actinides, tetravalent actinides have great affinity for electron-donor groups that bind Fe(III), and follow Fe(III) in mammalian iron transport and storage systems. The great affinity and specificity of the siderophores towards Fe(III) suggest that modification of siderophores, which are effective sequestering agents for ferric ion, would yield potential chelators of tetravalent actinides, which present significant biological hazards associated with nuclear technology. Following absorption, the actinide cations that have been inhaled, ingested, or deposited in a wound circulate in serum bound to transferrin (Tf), the iron transport protein, and renal and gastrointestinal excretion are severely inhibited. As actinide-containing cells and structures die, the released actinide is recirculated, and nearly all of it is re-deposited at new sites. The alpha particles emitted by the actinides kill cells and induce cancer in the major storage tissues-lung, bone, liver. The only known way to reduce the toxicity of these radioactive metals is to use chelating agents to accelerate their excretion, thereby preventing deposition or re-deposition. Normally, such actinide chelating agents will be octadentate ligands, as opposed to the generally hexadentate or tetradentate siderophores. Other uses, such as radionuclide chelation in nuclear medicine applications, for example, are also clearly possible.

The biomimetic approach of the present invention, which designs and synthesizes sequestering agents for ferric ion and actinides, are based on siderophores. The metal binding units of siderophores are usually either catechols (dihydroxybenzene analogues; Formula 1A) or hydroxamic acids (Formula 1B):

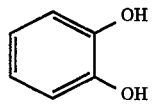

Formula 1A

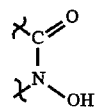

Formula 1B

In fact, desferrioxamine B (DFO), a tri-hydroxamic acid siderophore, is used as a human iron sequestering agent. This chelating agent has predominated for over 30 years as the method of choice for treatment of iron overload. However, DFO has low oral activity and a number of adverse effects: including administration via a cumbersome subcutaneous infusion, leading to poor patient compliance with the treatment regime, and poor efficacy in removing deposited actinides. As a result of these limitations of the prior art drugs, there is a need for more effective and orally active iron sequestering agents to treat iron overload as well as actinide poisoning.

The most potent natural Fe(III) chelator is enterobactin, a siderophore produced by enteric bacteria with a formation constant of $K_f \approx 10^{49}$, pM=35.5. This hexadentate ligand is composed of three catechoylamide groups attached to a tri-serine lactone backbone. Catecholates are much stronger sequestering agents than hydroxamate ligands, such as DFO, and these ligands are faster in removing iron from human transferrin, primarily for kinetic rather than thermodynamic reasons. Synthetic analogues of catechol-based siderophores are also known. However, there are a number or difficulties in developing catecholates into effective pharmaceutical agents. A number or catecholate siderophores, including enterobactin, will be bound by albumin in serum. They also strongly promote the growth of pathogenic microorganisms. The weak acidity of catechol and the required loss of two protons per catechol group at or about neutral pH limit the effectiveness of catechol-based ligands in vivo. These factors place severe limitations on the use of catechol-based ligands as therapeutic agents. It is therefore desirable to provide a medicinally useful metal chelating agent having a higher $K_a$, i.e., more acidic, and which therefore binds more effectively at physiological pH, than catechol-based compounds. Uninegative ligands, i.e., ligands having a single negative charge near neutral pH range, are particularly desirable, in contrast to the correspondingly highly charged ferric and plutonium catechol complexes.

Derivatives of hydroxypyridinones ("HOPO") are of particular interest, since these ligands selectively display high affinity for ferric and actinide ion. These ligands and their mono-anions have a zwitteronic resonance form that is isoelectronic with the catechol dianion. The abbreviation "HOOP" will hereinafter be used to include hydroxypyridinone analogues as well as isomers or tautomers thereof, in either protonated or deprotonated forms.

The HOPO ligands have been shown to be very promising sequestering agents. The bidentate 3,4-1HOPO ligand, 1,2-dimethyl-3-hydroxy-4-pyridinone, is orally active and has gone through extensive study, including clinical trials. However, there are many limitations for such a simple bidentate ligand. Multidentate HOPO derivatives have advantages over simpler bidentate ligands: in particular, low toxicity resulting from a higher binding affinity (pM) at low (clinical level) ligand concentrations.

Previous patents on hydroxypyridone ligands used as chelating agents include "Hydroxypyridonate Chelating Agents", U.S. Pat. No. 4,698,431, patented by Kenneth N. Raymond, Robert C. Scarrow, and David L. White, Oct. 6, 1987. This invention provided 1,2-HOPO derivatives with either an amide or a carboxylic acid moiety in the number 6 position. These chelating agents are useful in selectively removing certain cations from solution and are particularly useful as ferric ion and actinide chelators. However, U.S. Pat. No. 4,698,431, did not claim other chelating agents having 3,2-HOPO moieties incorporated within their structures or a carboxy moiety on the number 3 position of 1,2-HOPO ring.

Other related an includes Pharmaceutical Compositions of Hydroxypyridones, U.S. Pat. No. 4,666,927, patented by Robert C. Hider, George Kontoghiorghes, Jack Silver, and Michael A. Stockham, May 19, 1987. Claim 1 of this patent claims a number of possible chelating agents having 1,2-HOPO, 3,2-HOPO, or 3,4-HOPO moieties incorporated within their structures that are linked through a number of possible combinations of linking groups, including —CONH— groups. However, U.S. Pat. No. 4,666,927 teaches against a HOPO moiety having a substitution ortho to the hydroxy or oxo group of the HOPO ring.

In contrast to U.S. Pat. No. 4,666,927, the inventors have developed a new design strategy, that is to synthesize a new series of 3,2-HOPO derivatives with either a carboxylic acid or a (substituted) carbamoyl moiety substituted on the ring carbon ortho to the HOPO hydroxy group. The particular coordination geometry and the hydrogen bonding between the amide proton and HOPO oxygen donor in these HOPO-metal complexes disclosed by the present invention thereby make the new series of 3,2-HOPO derivatives unusually good complexing agents having very high stability and specificity towards metal binding. The inventors further found these new compounds have stronger acidity and chelating ability for iron and actinides and have high oral activity in removing toxic actinides in vivo.

Furthermore, the method of synthesizing the present invention having 3,2-HOPO moieties incorporated within their structures with the (substituted) carbamoyl group ortho to hydroxy group of HOPO ring is not obvious. One earlier attempt by the inventors included: reacting 4-carboxy-3-hydroxy-2(1H)-pyridinones (Formula 9A) with 1,1'-carbonyldiimidizole to produce the active amide intermediate, which is then reacted with backbone amines to form the corresponding novel 3,2-HOPO ligands, similar to the case of thiohydroxamate. See. e.g., Kamal Abu-Dari and Kenneth N. Raymond, "Ferric Ion Sequestering Agents. 23. Synthesis of Tris(hydroxypyridinethione) Ligands and Their Ferric Complexes; X-ray Structure Analysis of N,N',N''-Tris (1,2-didehydro-1-hydroxy-2-thioxopyrid-6-yl)carbonyl)-2, 2', 2''-triaminotriethylaminato)iron(III)," Inorg. Chem. 1991, 30, 519–524. However, the purification of the final product is difficult, therefore, this method is not preferred. A second attempt to carry out the above reaction produced the acid chloride of 1-alkyl-4-carboxy-3-hydroxy-2(1H)-pyridinone as an active intermediate using thionyl chloride or oxalyl chloride, similar to the case of catechoylamide ligands. Due to the low yield of compound in preliminary tests, this method is also not preferred.

The present invention discloses a process to synthesize the desired multidentate 1,2-HOPO and 3,2-HOPO ligands in good yield.

Accordingly the present invention comprises an effective multidentate siderophore analogue HOPO ligand in which one or more HOPO rings are linked to a molecular backbone through amide linkage. The inventors have previously reported the synthesis of siderophore analogues with linear, multipodal and macrocyclic topologies, and have shown a more effective ligand is one with a greater predisposition toward binding. In the design of the present invention, these synthetic strategies, as well as the binding abilities, solubility and lipophilicity of the resulted compounds, are important factors considered.

SUMMARY OF THE INVENTION

The present invention represents a breakthrough in siderophore-like ligands intended for pharmaceutical use. The present invention provides novel 1,2-HOPO and 3,2-HOPO chelating agents capable of selectively forming stable complexes with certain cations such as $Fe^{3+}$, $Gd^{3+}$, $Am^{3+}$, $Pu^{4+}$, $Np^{4+}$, and $U^{6+}$ ions.

The present invention allows this highly advantageous class of chemicals to be administered orally or by injection.

These complexing agents are lipophilic enough to display oral activity.

The present invention provides a method to produce these compounds safely and in good yield.

The present invention provides unusually good complexing agents with high stability and specificity for iron and actinides.

The present invention provides chelating agents which are relatively acidic and incorporate monoprotic ligand groups.

The present invention provides methods of using the novel chelating agents.

The present invention provides methods of synthesizing the novel chelating agents. These new HOPO ligands are generally synthesized by introducing a carboxylate group at the carbon atom ortho to the ligating group of HOPO ring, then making an amide linkage to a suitable molecular backbone.

In one aspect of the invention, novel chelating agents are provided which include HOPO-based bidentate and multidentate ligands, as well as mixed multidentate ligands such as HOPO-substituted desferrioxamine. In other aspects of the invention, novel methods of synthesizing the HOPO-derived chelating agents are provided, as are methods of using the novel compounds.

DETAILED DESCRIPTION OF THE INVENTION

Figure 1:
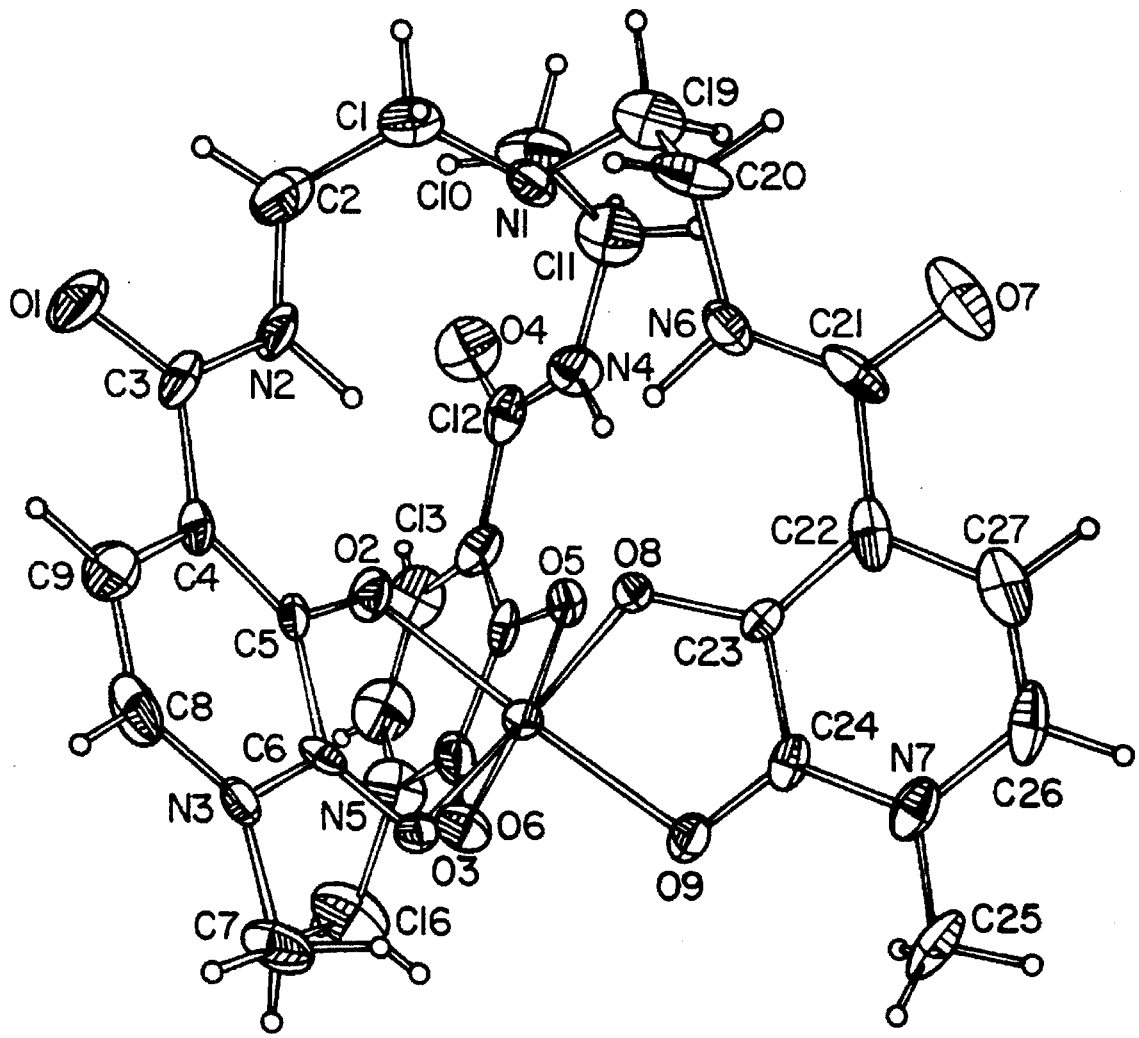
FIG. 1 is a diagram showing the crystal structure of the Fe(III)-TREN-3,2-HOPO complex.

The present invention provides novel 1,2-HOPO and 3,2-HOPO chelating agents capable of selectively forming stable complexes with certain cations such as $Fe^{3+}$, $Gd^{3+}$, $Am^{3+}$ and $Pu^{4+}$, $Np^{4+}$, and $U^{6+}$ ions. Accordingly the present invention comprises a compound consisting of 4-(substituted)carbamoyl-3-hydroxy-2-pyridinones having optional substituents on the nitrogen atom, and on one or more of the carbon atoms of the ring. Shown below are the preferred basic ring system in the compounds of the present invention (Formula 2), the basic ring system of 1,2-HOPO-6-carbamoylamide (Formula 3), and catechoylamide (Formula 4):

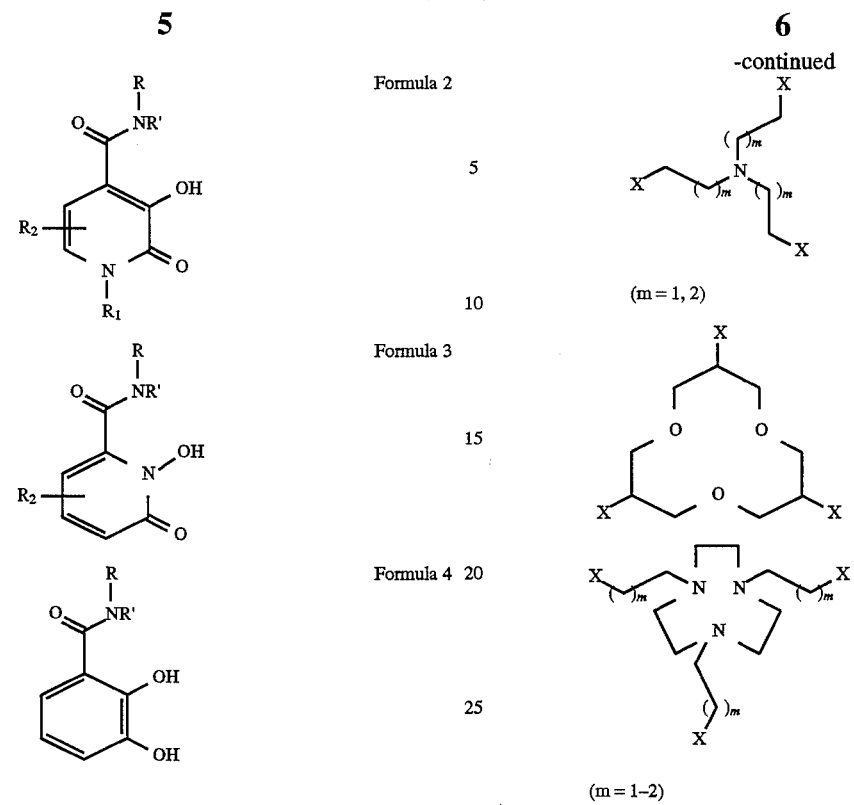

Formula 2

Formula 3

Formula 4 wherein $R_1$ and $R_2$ are separately selected from the group consisting of: hydrogen, $C_{1-4}$ aliphatic hydrocarbon groups, and $C_{1-4}$ aliphatic hydrocarbon groups substituted by a single halide, hydroxy, or carboxy group or an aryl group.

The HOPO rings are attached to a molecular or polymeric backbone R through amide linkages, where R is selected from multi-linking groups. Representative examples of such multi-linking groups include, but are not limited to:

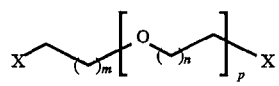

Formula 5A ($m = 1-3, n = 1-3, p = 1-3$)

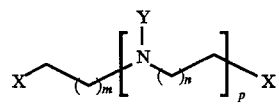

Formula 5B ($m = 1-3, n = 1-3, p = 1-3$)

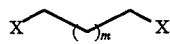

Formula 5C ($m = 1-6$)

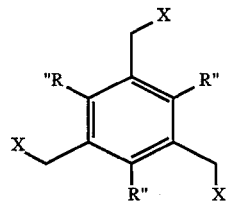

Formula 5D ($R'' = $ H, akyl)

Formula 5E ($m = 1, 2$)

Formula 5F

Formula 5G ($m = 1-2$)

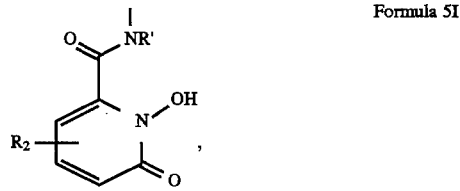

Formula 5H ($m = 2-6, q = 2-4$)

wherein the several X's of a formula may be a combination of chelating agents selected from the group consisting of:

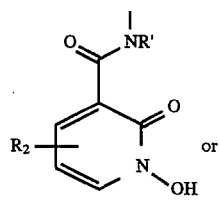

Formula 5I

Formula 5J or

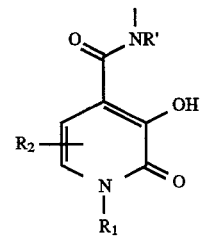

Formula 5K and Y is a 3,2-HOPO or 1,2-HOPO structural unit selected from the group consisting of:

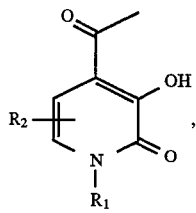
Formula 5L

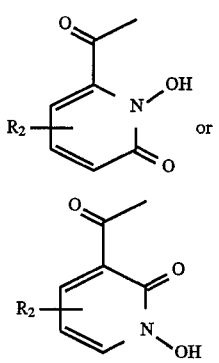
Formula 5M

Formula 5N where the free valency in each case indicates the preferred attachment point of the chelating group to a backbone.

In Formulae 5A to 5H, some of the chelating units X and Y may also be substituted by other chelating structural units. Representative examples of other chelating units include, but are not limited to: aminoacetic acid, hydroxamic acid, catechol, 2,3-dihydroxyterephthalamide or 3,4-HOPO.

Due to the presence of electron-withdrawing substituted carbamoyl group ortho to the hydroxy group of HOPO ring, compounds of Formulae 3 and 4 have lower $pK_a$s and more preferable coordination properties than corresponding HOPO ligands without the carbamoyl substituents. Their ring systems are also more able to withstand reduction or oxidation than corresponding HOPO ligands without the carbamoyl substituents. Similar to the case of catechoylamide complexes (Formula 6) and 1,2-HOPO-6-ylamide complexes (Formula 7), the strong hydrogen bonding between the amide proton and the adjacent oxygen donor, the hydroxy oxygen atom, also enhances the stability of the 3,2-HOPO complexes of this invention (Formula 8) as shown below:

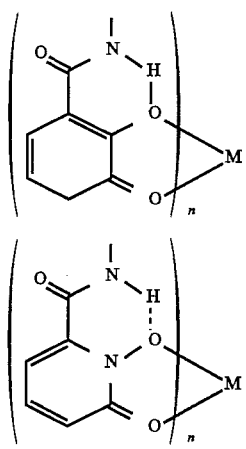
Formula 6

Formula 7

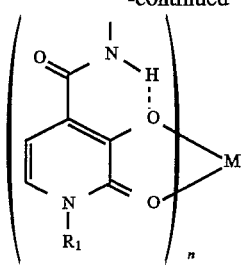
Formula 8 wherein M is a metal ion with a high charge to radius ratio and the free valency in each case indicates the preferred attachment point of the chelating group to a backbone.

These chelating agents become very powerful chelators for metal ions with high charge to radius ratios.

Another important feature of the 3,2-HOPO ligands of this invention is that these compounds have a terminal $R_1$ group substituted on the HOPO ring nitrogen, which provides certain adjustable lipophilicity to the whole molecule, necessary for the ligand to display oral activity.

The lipophilic properties of the HOPO substituted compounds in combination with their relatively low $pK_a$s make them effective oral agents, a highly desirable property for therapeutic agents. The new 3,2-HOPO compounds display high binding constants for ferric ion, on the order of $10^{26}$ to $10^{29}$ $M^{-3}$, and pM values from 19 to 27 for the Fe(III)-tris (HOPO) complexes and are thus effective ligands for iron as well as for certain other ions with similar coordination properties (e.g., the actinide(IV) ions). These ligands are also surprisingly good chelating agents for the lanthanides.

Monomeric bidentate compounds of the invention include those given by the structure of Formula 9A, 9B and 9C.

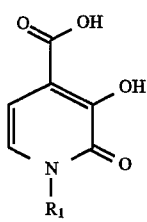
Formula 9A

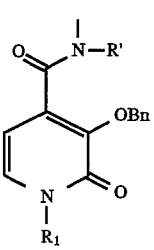
Formula 9B

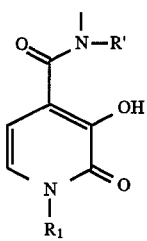
Formula 9C

Formula 9A shows the acid form, while Formulae 9B and 9C show the benzyl protected amide form and deprotected amide form respectively. In these forms, $R_1$ is selected from the group consisting of: hydrogen, $C_{1-4}$ aliphatic hydrocarbon groups, and $C_{1-4}$ aliphatic hydrocarbon groups substituted by a single halide, hydroxy, or carboxy group or an aryl group. When $R_1$ is selected from these groups, the molecule is provided with adjustable lipophilicity. In Formula 9B and 9C, R' is selected from the group consisting of: hydrogen, $C_{1-8}$ aliphatic hydrocarbon groups, and $C_{1-8}$ aliphatic hydrocarbon groups substituted by a single carboxy, sulpho, sulphamoyl, N-methyl or N-ethyl sulphamoyl group, or an aryl group. The free valency in each case indicates the preferred attachment point of the chelating group to a backbone. Optionally, formulae 9A and 9C are in the form of a physiologically acceptable salt.

Although the new HOPO monomers display high affinity for ferric ions, for example, 1-methyl-4(1-propylcarbamoyl)-3-hydroxy-2(1H)-pyridinone (Formula 9C, backbone=n-propyl, R'=H, $R_1$=methyl), it has overall complex binding constants on the order of $10^{28.7}$ $M^{-3}$ for Fe(III). However, because of the 3:1 stoichiometry of the bidentate monomer/Fe complex, its stability is strongly dependent on its concentration (by the 3rd power). Generally, the pM concept was used to define the concentration of unchelated metal ion at physiological pH (7.4), and at chelator and metal ion concentrations (μmolar range) which are those expected in the plasma of a chelator-treated patient. The more effective chelator has the larger pM value. Since the multidentate 3,2-HOPO ligands have higher pM values than their bidentate analogues, they have stronger scavenging power for iron and actinides in vivo. For example, the bidentate compound 1-methyl-4(1-propylcarbamoyl)-3-hydroxy-2(1H)-pyridinone has a pM of 19.26 for Fe(III), while the hexadentate compound TREN-Me-3,2-HOPO (Formula 12, m=1) has a pM of 26.69 for Fe(III).

Tetradentate chelating agents of the present invention, which incorporate two 3,2-HOPO structural units, are given by Formula 10. These compounds form stable 2:1 complexes with actinides, and are promising actinide sequestering agents.

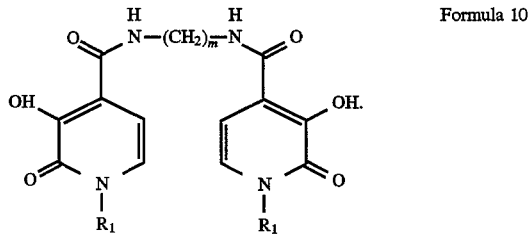

Formula 10

In Formula 10, two 3,2-HOPO structural units are linked to an aliphatic hydrocarbon molecular backbone —$(CH_2)_m$—, $R_1$ is as given above for the monomers of Formula 9, and m is an integer from 2 to 9. In a particularly preferred form, m is five, and the structure is "5-LI-Me-3,2HOPO" (1-Methyl-3-hydroxy-2(1H)-pyridinone structures separated by five methylene groups, some-what analogous in structure to previously known 5-LICAM, i.e. linear catechoylamide sequestering agents). Alternative molecular backbones of special interest are groups corresponding to a hydrocarbon group in which one or more carbon atoms are replaced by an oxygen or nitrogen atom. Such backbones are preferably more hydrophilic and the corresponding ligands will have better solubility in water. Specific examples of such tetradentate ligands are given by Formula 11, in which $R_1$ is as given above for the

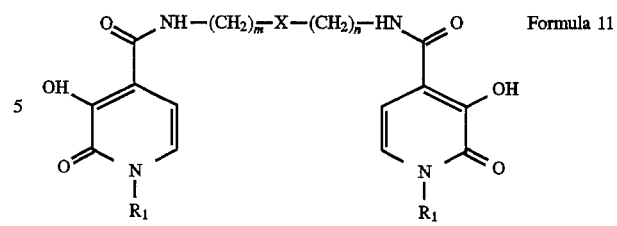

Formula 11 monomers of Formula 9, and m and n are each an integer front 2 to 4, and X may be oxygen or nitrogen (with a hydrogen, alkyl or aryl substitution).

Since hexadentate chelating agents form 1:1 complexes with iron, their stability has first order dependence on the ligand concentration. In other words, the hexadentate 3,2-HOPO ligands have strong scavenging power for iron at low concentration of ligand. The inventors surprisingly notice that the new tetradentate and hexadentate 3,2-HOPO ligands are not only excellent iron sequestering agents but also excellent actinide sequestering agents in vivo. This is surprising because actinides have coordination numbers greater than eight and therefore would not be expected to bind well to tetradentate or hexadentate chelating agents. This is not the case for tetradentate CAM or 1,2-HOPO sequestering agents, which are toxic and less effective in vivo.

Furthermore, because the new HOPOs are such effective chelators, it is possible that they can be used as MRI diagnosis complexing agents. As a specific example, see example 20, infra.

Hexadentate chelating agents of the present invention which incorporate three 3,2-HOPO structural units with a tripodal amine backbone are given by Formula 12 and 13. In both Formulae, $R_1$ is as given above for the monomers of Formula 9; and in Formula 12, m is an integer from 1 to 3.

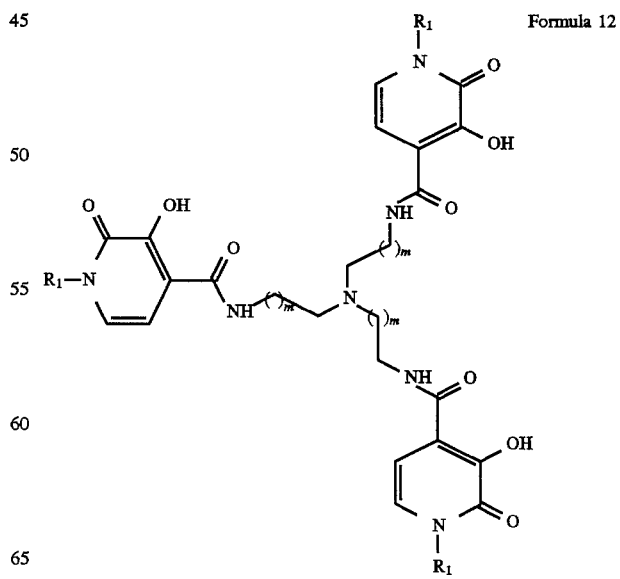

Formula 12

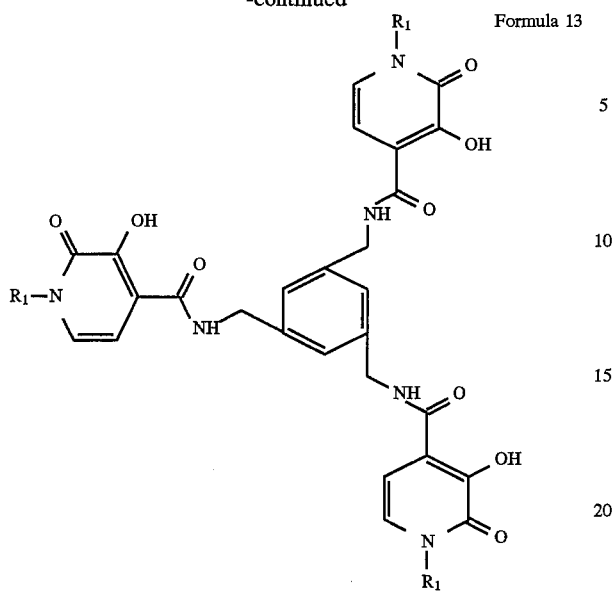

Formula 13

The chelating agents of this invention also include mixed HOPO ligands which in addition to having at least one 3,2-HOPO structural unit, 1nay also have other chelating structural units. Examples of these mixed chelating agents given by Formulae 15–17.

Compounds of Formula 12 with m=1 represents a particularly preferred embodiment of the invention, as it has been demonstrated to be non-toxic and extremely effective both in ferric chelation and in the decorporation of actinides such as Pu(IV), Am(III) and U(VI). This structure is abbreviated as TREN-Me-3,2-HOPO, similar in structure to previously known triscatechoylamide ligand TRENCAM.

Octadentate chelating agents provided by the present invention which incorporate four 3,2-HOPO structural units are given by Formula 14. This design is based on the siderophore analogues with 'H' shaped tetrapodal topology developed by the inventors, which proved to be predisposed towards metal binding. These chelating agents are especially suitable for binding actinide (IV) ions, because of their preferred high coordination number (eight or greater).

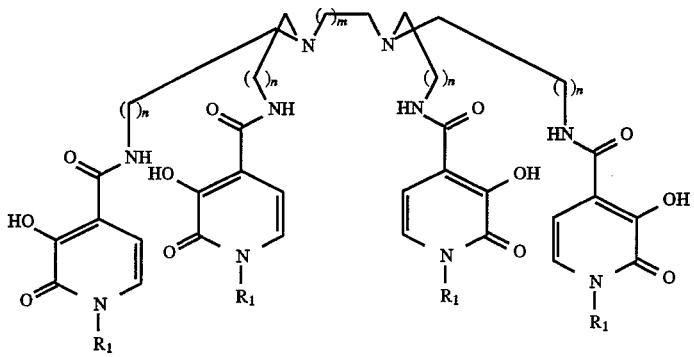

Formula 14

In Formula 14, $R_1$ is as given above for the monomers of Formula 9, and m and n are each an integer frown 1 to 4.

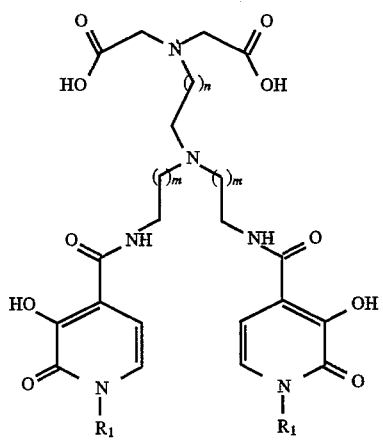

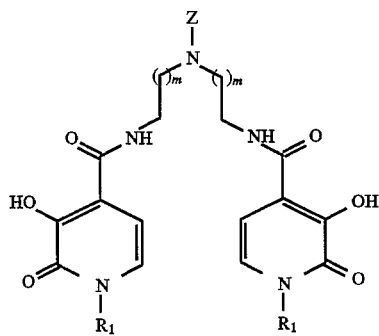

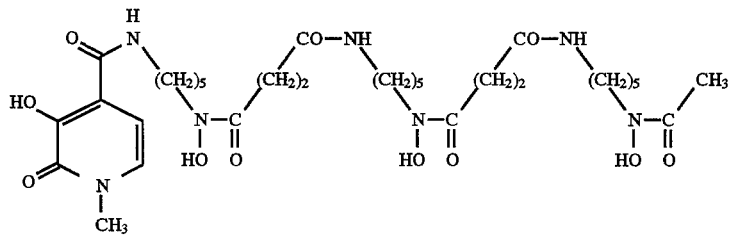

Formula 15 gives a 3,2-HOPO-substituted analogue of ethylenediamine-N,N,N',N'-tetraacetic acid (EDTA) and Formula 16 gives a 3,2-HOPO substituted diethylenetriamine analogue with the Z moiety which is selected from the group consisting of: hydrogen, $C_{1-4}$ hydrocarbon groups, 2-hydroxyethyl, 2-aminoethyl, and $C_{1-4}$ aliphatic hydrocarbon groups substituted by a single carboxy, sulpho, acrylamido or an aryl group; Formula 17 gives a 3,2-HOPO-substituted analogue of desferrioxamine-B. In Formulae 15–17, $R_1$ is also as given above for the monomers of Formula 9. The chelating agent of Formula 16 with a long hydrocarbon chain as the Z group is a promising extractant for actinides, especially Am(III).

The chelating agents of this invention also include amine compounds which, in addition to having at least one 3,2-HOPO structural unit, are also substituted with 1,2-HOPO analogues and catechol analogues. Thus, in the compounds of Formulae 10–16 above, the HOPO substituents could be replaced with the any of the structures given by Formulae 18 to 21, as long as one or more 3,2-HOPO substituents remain present on the chelating structure (where the free valency in each case indicates the preferred attachment point of the chelating group to a backbone).

Formula 15

Formula 16

Formula 17

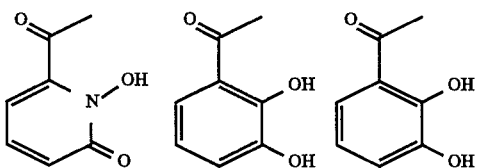

Formula 18   Formula 19

Formula 20

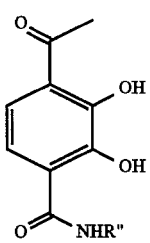

Formula 21

Also included in the present invention are chelating agents having polymeric backbones and at least one amine functionality to which a HOPO substituent is bonded through an amide-type linkage. Examples of suitable polymers here include, but are not limited to, poly(styrenedivinylbenzene), agarose, and polyacrylamide.

The present invention also relates to novel methods of synthesizing the aforementioned chelating agents as outlined below.

The novel 3,2-HOPO compounds (represented below by the monomeric compound) 4 shown in Formula 9–17 may be conveniently synthesized according to Scheme 1.

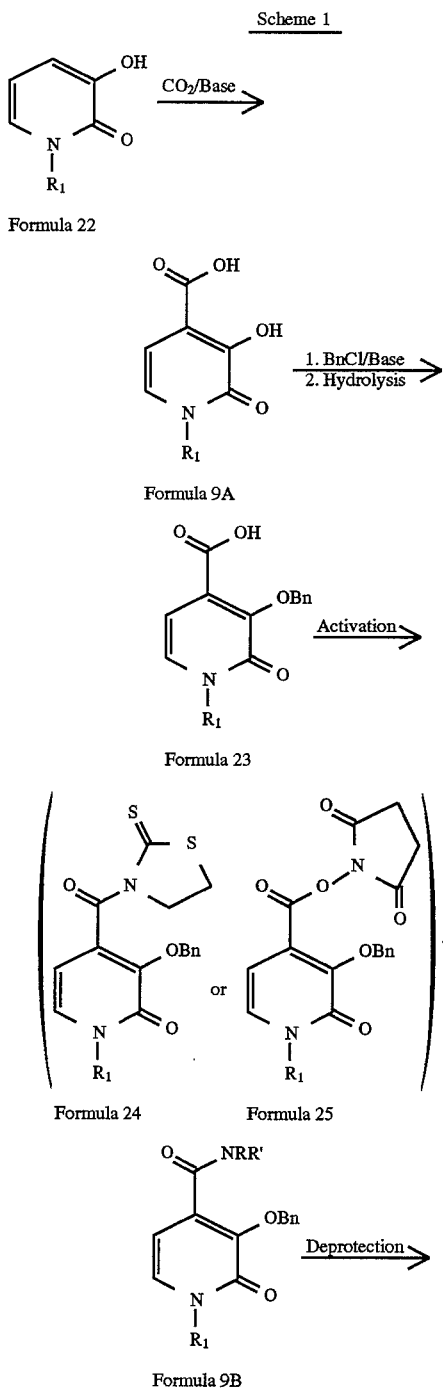

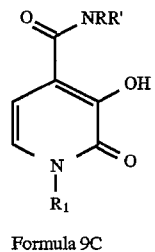

Formula 9C

Wherein R=backbone, $R_1$ is selected from the group consisting of: hydrogen, $C_{1-4}$ aliphatic hydrocarbon groups, and $C_{1-4}$ aliphatic hydrocarbon groups substituted by a single halide, hydroxy, or carboxy group or an aryl group, and R' is selected from the group consisting of: hydrogen, $C_{1-8}$ aliphatic hydrocarbon groups, and $C_{1-8}$ aliphatic hydrocarbon groups substituted by a single carboxy, sulpho, sulphamoyl, N-methyl or N-ethyl sulphamoyl group, or an aryl group.

The 4-carboxylic acid derivative (Formula 9A) of 1-alkyl-3-hydroxy-2-pyridinone is prepared from a 1-alkyl-3-hydroxy-2-pyridinone. The latter, for example, 1-methyl-3-hydroxy-2-pyridinone (Formula 22, $R_1$=methyl) is a known compound. However, the reported procedure is not safe and is neither convenient nor suitable for large scale production. The reported procedure is to put 3-hydroxy-2(1H)-pyridinone and iodomethane in a sealed glass tube and heat this mixture to 140° C. for two days. However, the size of the sealed glass tube is limited and yields only several grams of product. Furthermore, the pressure in the sealed glass tube may cause it to explode, thereby releasing toxic fumes. If the glass tube does not explode, the resultant material is treated with gaseous sulfur dioxide, a corrosive and toxic gas. In the final step, the compound is purified by recrystallization from petroleum ether, a method that is not safe, not convenient and is time consuming. Because Formula 9A is an important precursor to the present invention, the inventors have developed a safe and convenient procedure which can be used for large scale production as follows. 3-Hydroxy-2(1H)-pyridinone and iodomethane (1:1.5 tool ratio) are placed in a capped Teflon container, the container is put in a stainless steel Parr bomb and heated to 150° C. for 2 days. This container may be 50 times larger than the sealed glass tube and will not explode. The cooled bomb is opened and the resultant thick dark oil is mixed with sodium sulfite (1:1.5 mol ratio), which is not corrosive and toxic (as is gaseous sulfur dioxide) and dissolved in water. The solution is neutralized and then extracted with a suitable solvent. The 1-methyl-3-hydroxy-2-pyridinone may then be purified with a flash silica gel plug, which is much safer, convenient and time saving than recrystallization from hot petroleum ether. The reported procedure yields approximately 6 grams each batch. The present invention can yield approximately 304) grams by using a 1 liter capacity Parr bomb each time.

The 4-carboxylic acid shown in Formula 9A ($R_1$=H, alkyl) may then be prepared from the 3,2-HOPO compound of Formula 22 ($R_1$=H, alkyl) as follows. A quantity of the 3-hydroxy-2(1H)-pyridinone is mixed with anhydrous alkali metal carbonate, such as sodium or potassium carbonate, in a preferred mol ratio of 1:3 to 1:5. The dried mixture is then put in a Parr bomb and the bomb is then filled with dry carbon dioxide (850 psi) and heated to 170–200° C. for 2 days. The cooled bomb is opened and the resultant solid is dissolved in water and treated with HCl, the 4-carboxylic acid may then be isolated as free acid form e.g. by filtration recrystallization and dried (see Example 1).

The 3,2-HOPO ligands shown in Formulae 9C to 17 may be preferably prepared from the reaction of an amine backbone and the active protected intermediates. Thus the 1-alkyl-4-carboxy-3-hydroxy-2(1H)-pyridinone (Formula 9A) may conveniently be converted to the protected acid (Formula 23) through the protection of the 3-hydroxy group. Protection can be performed with an ether group, such as a benzyloxy group or a methoxy group. Benzyloxy protection is preferred because it can be easily deprotected by hydrogenation. Reaction of the protected acid with a compound to activate the acid (for example: 2-mercapto-thiazoline or N-Hydroxysuccinimide (NHS)), in the presence of 1,3-dicyclohexylcarbodiimide (DCC) gives the activated intermediates (Formulae 24 or 25). This is reacted with the amine compound which will provide the "backbone" of the chelating agent at room temperature to give the protected 3,2-HOPO ligands generally as viscous oils. They are purified preferably by extraction and/or column chromatography. The hydroxy protecting groups may then be removed by hydrogenation and the final product may be recrystallized from methanol, ethyl acetate, or water.

The 3-benzyloxy-1-methyl-4-(2-thioxothiazolidin-1-yl) carbonyl-2(1H)-pyridinone (Formula 24) is a highly preferable intermediate: it is a bright yellow crystalline compound, easy to be prepared and purified. Unlike other activated intermediates such as 3-benzyloxy-1-methyl-4-(succinimidyloxy)carbonyl-2(1H)-pyridinone (Formula 25), it is stable and not sensitive to alcohol, water, or even dilute inorganic acid and base. It selectively reacts with primary amines to form amide products. The end of the reaction can be easily monitored by the disappearance of its characteristic yellow color.

While many amines can be used in this reaction to effect production of 3,2-HOPO-substituted chelating agents, preferred amines are those which correspond to the structures of Formulae 9–17. Particularly preferred amines are the polyamines: 1,5-diaminopentane ($NH_2(CH_2)_5NH_2$), 2,2'-oxybis(ethylamine), tris(2-aminoethyl)amine (see Formula 12, m=2), tris(aminomethyl)-benzene (see Formula 13), N,N,N',N'-tetra(2-aminoethyl)ethylenediamine, also known as PENTEN (see Formula 14, me=n=2), and the monoamine desferrioxamine B (see Formula 17).

Other amines which may be used in the above synthetic procedure include compounds generally given by Formulae 10–13 but having one or more 1,2-HOPO, 3,2-HOPO and catechol moieties in addition to at least one 3,2-HOPO moiety. Organic polymers having at least one amino group may also be used (e.g., agarose, polyacrylamide, polystyrene derivatives and other similar compounds).

The novel 3,2-HOPO compounds (represented below by the monomeric compound) shown in Formula 9–17 are also conveniently synthesized according to Scheme 1-1.

Scheme 1-1

Step 1:

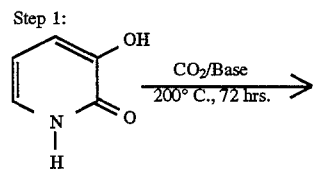

Formula 22A

-continued
Scheme 1-1

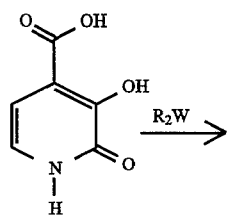

Formula 9A'

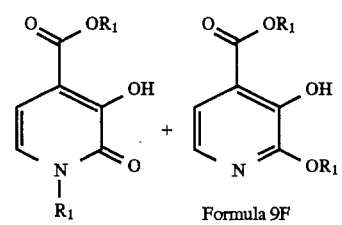

Formula 9E     Formula 9F

Step 2A:

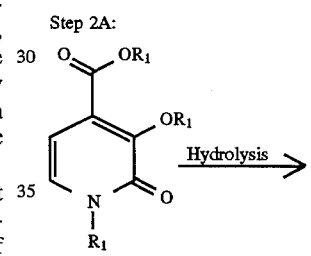

Formula 9E

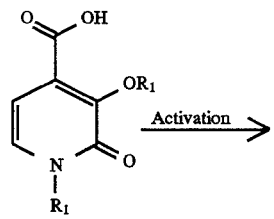

Formula 23A

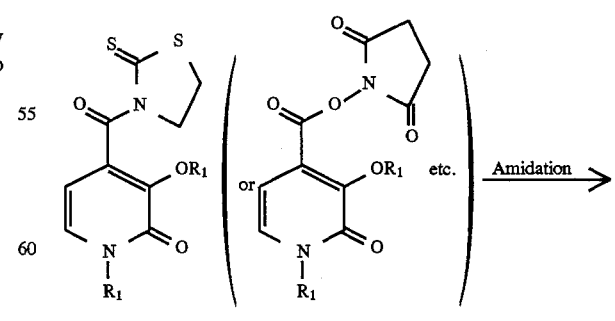

Formula 24A     Formula 25A

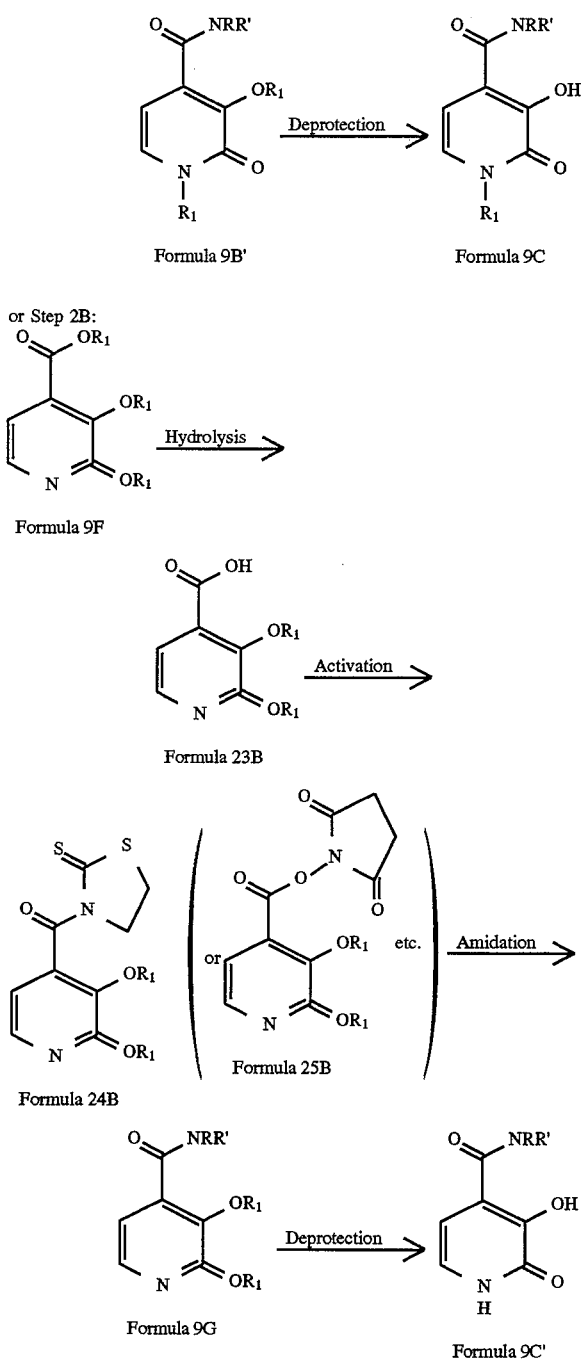

Wherein R=backbone, $R_1$ is selected from the group consisting of: hydrogen, $C_{1-4}$ aliphatic hydrocarbon groups, and $C_{1-4}$ aliphatic hydrocarbon groups substituted by a single halide, hydroxy, or carboxy group or an aryl group, and R' is selected from the group consisting of:

hydrogen, $C_{1-8}$ aliphatic hydrocarbon groups, $C_{1-8}$ aliphatic hydrocarbon groups substituted by a single carboxy, sulpho, sulphamoyl, N-methyl or N-ethyl sulphamoyl group, or an aryl group, and W is generally Chloride, Bromide, or Iodide.

Step 1: The 4-carboxylic acid shown in Formula 9A' is prepared from the commercially available 2,3-dihydroxypyridine (Formula 22 A) as follows. A quantity of the 3-hydroxy-2(1H)-pyridinone is mixed with anhydrous potassium carbonate in a preferred mol ratio of 1:3 to 1:5. The dried mixture is then put in a Parr bomb and the bomb is then filled with dry carbon dioxide (850 psi) and heated to 200° C. for 2 days. The cooled bomb is opened and the resultant solid is dissolved in water and treated with HCl, the 4-carboxylic acid is then isolated in a free acid form, for example, by filtrating recrystallizing and drying.

The 3,2-HOPO ligands shown in Formulae 9C to 17 are preferably prepared from the reaction of an amine backbone and the active protected intermediates. Thus the 4-carboxy-3-carboxy-3-hydroxy-2(1H)-pyridinone (Formula9A') is conveniently converted to the fully protected ester (Formula 9E and 9F) through the reaction with an alkylating agent, such as benzyl chloride or methyl iodide, in the presence of a base, such as potassium carbonate. 6 Compounds 9E and 9F are easily separated by column chromatography.

Step 2A: Compound 9E is converted into the protected acid (Formula 23A), and reaction of the protected acid with a compound to activate the acid (for example: 2-mercapto-thiazoline or N-Hydroxysuccinimide (NHS)) in the presence of 1,3-dicyclohexylcarbodiimide (DCC) gives the activated intermediates (Formulae 24 A or 25A). This is reacted with the amine compound which will provide the "backbone" of the chelating agent at room temperature to give the protected 3,2-HOPO ligands generally as viscous oils. They are purified preferably by extraction and/or column chromatography. The hydroxy protecting groups are then removed by deprotection (for example using $BBr_3$ as a deprotecting agent) and the final product is recrystallized from methanol, ethyl acetate, or water.

Step 2B: Similarly, compound 9F is converted into the protected acid (Formula 23B), and reaction of the protected acid with a compound to activate the acid (for example: 2-mercapto-thiazoline or N-Hydroxysuccinimide (NHS)), in the presence of 1,3-dicyclohexylcarbodiimide (DCC) gives the activated intermediates (Formulae 24 B or 25B). This is reacted with the backbone amine compound at room temperature to give the protected 3,2-HOPO ligands generally as crystalline solids. They are purified preferably by extraction and/or column chromatography. The hydroxy protecting groups are then removed by deprotection (for example using $BBr_3$ as a deprotecting agent) and the final product may be recrystallized from methanol, ethyl acetate, or water. In this way a series of N-unprotected multidentate 3,2-HOPO ligands can be prepared conveniently.

Properties of the Novel Compounds

Physical Properties:

The novel 3,2-HOPO compounds are white to pale-yellow in color. They are not hygroscopic in general and are obtained as micro-crystalline or amorphous solids. The monomers melt sharply, but the multidentate compounds decompose slowly upon heating. The most distinctive feature of their NMR spectra is the presence of two doublets in the aromatic region arising from the HOPO ring protons. The two doublets appear at d 6.4–6.6 and at d 6.6–7.2 ppm. The I.R. of the isolated compounds display a strong band at 1650–1680 cm-1 due to the amide group. In addition to that band here are four strong bands in the region 1430–1600 $cm^{-1}$ due to the ring C=C and C—N stretching frequencies.

Chemical Properties:

The 3,2-HOPO based amide compounds are in general slightly to moderately soluble in water, except the simple monomers, such as compound 1-methyl-4(1-propylcarbamoyl)-3-hydroxy-2(1H)-pyridinone (Formula 9C, R=1-propyl, R'=H), which is very soluble in water as well as organic solvents. They are nearly neutral (having pK$_a$'s on the order from 5 to 8), and the pH of saturated solutions typically are close to neutral. These compounds form stable complexes with various metal ions, such as Fe$^{3+}$, Gd$^{3+}$, Am$^{3+}$, Pu$^{4+}$, etc.

Experimental Methods

Infrared spectra were obtained with a Perkin-Elmer Model 283 spectrophotometer. The NMR spectra were obtained using UCB 250 (250 MHz), BVX 300 (300 MHz) and AM 500 (500 MHz) spectrometers. Mass spectral data were obtained with an Atlas MS11; a consolidated 12-110B, or a Kratos MS-50 spectrometer. The data can be tabulated as m/e. Elemental analyses were performed by the microanalytical Laboratory, Department of Chemistry, University of California, Berkeley.

3 Tris(3-aminopropyl)amine, 1,3,5-tris(aminomethyl) benzene, N,N,N',N'-tetrakis(2-aminoethyl)-ethylenediamine (PENTEN or H(2,2)-amine) can be prepared by methods described in the literature. N,N,N',N'-Tetrakis(2-aminoethyl)-1,3-propylenediamine (H(3,2)-amine), and N,N,N',N'-tetrakis(2-aminoethyl)-1,4-butylenediamine (H(4,2)amine) can be prepared in a manner similar to the preparation of PENTEN. Desferrioxamine B can be obtained from Ciba-Geigy. Other reagents and items disclosed can be purchased from Aldrich Chemical Co. and used as received.

Animal studies were completed using methods detailed in Radiation Protection Dosimetry, in press, P. W. Durbin et al., "In Vivo Chelation of Am(III), Pu(IV), Np(V) and U(VI) in Mice by TREN-(Me-3,2-HOPO)"; Radiation Protection Dosimetry, 17, No. 1, 1989, p. 351, P. W. Durbin et al., "Removal of $^{238}$Pu(IV) from Mice by Polycatechoylate, -Hydroxamate or -Hydroxypyridinonate Ligands"; Radiation Research, 99, 1984, p. 85, P. W. Durbin et al., "Specific Sequestering Agents for the Actinides . . . "; Radiation Research, 99, 1984. p. 106, P. W. Durbin et al., "Removal of Pu and Am from Beagles and Mice . . . "; Radiation Research, 81, 1980, p. 170, R. D. Lloyd et al., and P. W. Durbin et al., "Specific Sequestering Agents for the Actinides . . . ". The foregoing articles are hereby incorporated by reference.

Radionuclides used in the animal studies came from a variety of sources. However, they can be purchased commercially. The $^{238}$Pu(IV) citrate and $^{241}$Am(III) citrate solutions were prepared for animal injection by 8- to 10-fold dilution with 0.14M NaCl (pH 4) of concentrated stock solutions (0.08M sodium citrate buffer) that had been held in frozen storage at Lawrence Berkeley Laboratory (hereinafter LBL) for several years. [The $^{238}$Pu(IV) was originally obtained from D. R. Atherton at the University of Utah Radiobiology Laboratory, Salt Lake City. The $^{241}$Am (III) solution had been obtained many years earlier from the LBL Actinide Chemistry group.]

The $^{237}$Np(V) was obtained front J. Bucher of the LBL Actinide Chemistry group as NpO$_2$Cl in 0.1M HCl. It was diluted to the desired radioactivity concentration in 0.14M NaCl and the pH was adjusted to about 4.5 with NaOH just before use.

The $^{232}$U was obtained from the Isotope Products Laboratory, Burbank, Calif., and $^{234,235}$U was obtained as U metal from long held LBL storage. The two U sources were combined and dissolved in 6N HNO$_3$, dried, and redissolved in 0.1N HCl. The daughter radioactivities were removed by elution from a Dowex-50×4 column (22 cm length, 0.7 cm diameter, 1.5 mL.min$^{-1}$ flow rate) with 3.2N HCl. The U fractions (previously identified by a trial run with $^{234,235}$U alone) were combined, dried, and redissolved in 0.14M NaCl at pH 5.5.

All injections solutions, alter dilution and pH adjustment, were sterilized by passing through a 0.22 lain Millipore flier into 10 mL serum bottles fitted with rubber stoppers, and frozen until used.

Solutions were calibrated by alpha scintillation counting (Packard Tri-Carb 460C, Ecolume® scintillation fluid).

The current catalogue of Isotope Products Laboratory, Burbank, Calif., lists for retail sale: $^{238}$Pu, $^{241}$Am, $^{237}$Np, and $^{232}$U.

EXAMPLES

Example 1

Preparation of 3-benzyloxy-4-carboxy-1-methyl-2(1H)-pyridinone and related precursors (1) 1-Methyl-3-hydroxy-2(1H)-pyridinone (Formula 22, R$_1$=methyl):

1-methyl-3-hydroxy-2(1H)-pyridinone is a known material; however the previous procedure for preparation is neither safe nor suitable for large scale production. Therefore, the inventors have developed a safe and convenient procedure which can be used for large scale or industrial production after minor modification. The details are described as follows:

3-hydroxy-2(1H)-pyridinone (34.44 g, 0.31 mol) and iodomethane (75 g, 0.53 mol) are placed in an 80 mL capped Teflon container (Caution: iodomethane is highly toxic), and put in a stainless steel Parr bomb and heated to 150° C. for about 48–60 hours. The cooled bomb is opened and the excess iodomethane decanted. The resultant thick dark oil is mixed with sodium sulfite (64 g, 0.5 mol) and dissolved in 300 mL water to form a pale brown solution. The solution is neutralized to pH 7–8 and filtered to remove any insoluble impurity. The filtrate is then extracted with methylene chloride (4×100 mL). The combined extracts are dried, then applied to a flash silica gel plug (6 cm×8 cm) and eluted with 4% methanol in methylene chloride. The solvent is rotary evaporated to give the title compound (24.3 g, 62.6%) as colorless crystals, mp. 129°–130° C. 1H NMR (250 MHz, CDCl$_3$): δ3.621 (s, 3H), 6.144 (t, 1H, J=7.10), 6.79–6.85 (m, 2H), 7.27 (s,br, 1H). Anal. for C$_6$H$_7$NO$_2$ (125.129), Calcd. (found): C, 57.59 (57.23); H, 5.64 (5.70); N, 11.20 (10.93).

(2) 4-Carboxy-1-methyl-3-hydroxy-2(1H)-pyridinone (Formula 9A, R$_1$=methyl)

1-Methyl-3-hydroxy-2(1H)-pyridinone (1) (6.25 g, 50 mmol) is mixed with anhydrous potassium carbonate (36 g, 0.26 mol). The vacuum dried mixture is put in a Parr bomb which is then filled with dry carbon dioxide gas (850 psi) and heated to 175°–185° C. for 3 days. The cooled bomb is opened and the resultant pale yellow solid is dissolved in ice water and acidified with 6N HCl to produce a beige crystalline product (7.42 g, 87.5%), m.p. 243°–245° C. (dec). $^1$H NMR (250 MHz, DMSO-d$_6$): δ3.469 (s, 3H), 6.357 (d, 1H, J=7.33), 7.166 (d, 1H, J=7.19), 7.27 (s,br, 1H). $^1$H NMR (250 MHz, D$_2$O-NaOD): d 3.342 (s, 3H), 6.176 (d, 1H, J=6.94), 6.487 (d, 1H, J=7.00). Anal. for C$_7$H$_7$NO$_4$ (169.14): Calcd. (found): C, 49.71 (49.74); H, 4.17 (4.30); N 8.28 (8.16).

(3) 3-Benzyloxy-4-carboxy-1-methyl-2(1H)-pyridinone (Formula 23, R$_1$=methyl)

4-Carboxy-1-methyl-3-hydroxy-2(1H)-pyridinone (6.8 g, 0.04 mol) is mixed with benzyl chloride (12.1 g, 0.088 mol), anhydrous potassium carbonate (13.8 g, 0.1 mol) in anhydrous dimethyl-formamide (DMF) (120 mL). The mixture is heated at 75°–80° C. under $N_2$ in darkness for 16 hours. The reaction mixture is filtered and rotary evaporated to yield a dark oil, which is purified by a silica gel plug as mentioned in 1-methyl-3-hydroxy-2(1H)-pyridinone to give the 3-benzyloxy-4-benzyloxycarbonyl-1-methyl-2(1H)-pyridinone as a pale yellow, thick oil. It is mixed with methanol (50 mL) and a 6M NaOH solution (10 mL). The mixture is stirred at room temperature for 4 hours, then evaporated to dryness. The residue is dissolved in water (100 mL), and acidified with 6M HCl solution to pH 2 to give the title compound (9.3 g 88.7%), as a white crystalline product, m.p. 152°–153° C. $^1$H NMR(250 MHz, $CDCl_3$): δ3.616 (s, 3H),5.611 (s, 2H), 6.695 (d, 1H, J=7.13),7.152 (d, 1H, J=7.16), 7.35–7.48 (m, 5H). Anal. for $C_{14}H_{13}NO_4$. $0.2H_2O$ (262.87), Calcd. (found): C, 63.97 (64.05); H, 5.14 (5.14); N, 5.33 (5.18).

Example 2

Preparation of 3-benzyloxy-1-methyl-4-(2-thioxothiazolidin-1-yl)carbonyl-2(1H)-pyridinone (Formula 24, $R_1$=methyl)

To a solution of 3-benzyloxy-4-carboxy-1-methyl-2(1H)-pyridinone (1.05 g, 4 mmol), 2-mercaptothiazoline (0.50 g, 4.2 mmol) and a catalytic amount of 4-dimethylaminopyridine (DMAP) in dry methylene chloride (50 mL), N,N'-dicyclohexylcarbodiimide (DCC) (0.86 g, 4.2 mmol) is added. After stirring for 4 hours, the dicyclohexylurea (DCU) solids are removed by filtration, the yellow filtrate is rotary evaporated to give a yellow solid. Crystallization from isopropanol-methylene chloride gives the title compound (1.16 g, 80.4%) as bright yellow crystalline plates, m.p. 149°–150° C. $^1$H NMR (250 MHz, $CDCl_3$) δ2.867 (t, 2H, J=7.32), 3.594 (s, 3H), 4.313 (t, 2H, J=7.33), 5.301 (s, 2H), 6.107 (d, 1H, J=6.99), 7.126 (d, 1H, J=7.00), 7.31–7.45 (m, 5H). Anal for $C_{17}H_{16}N_2O_3S_2$ Calcd. (found): C, 56.64 (56.36); H, 4.47 (4.47); N, 7.73 (7.73); S, 17.78 (17.41).

Example 3

Preparation of 3-hydroxy-1-methyl-4(1-propylcarbamoyl)-2(1H)-pyridinone (Formula 9C, $R_1$=methyl, R=n-propyl, R'=H)

(1) 3-Benzyloxy-1-methyl-4(1-propylcarbamoyl)-2(1H)-pyridinone (Formula 9B, $R_1$=methyl, R=n-propyl, R'=H)

To a solution of 3-benzyloxy-1-methyl-4-(2-thioxothiazolidin-1-yl)carbonyl-2(1H)-pyridinone (720 mg, 2 mmol) in dry methylene chloride (40 mL) is added n-propylamine (0.18 mL, 2.2 mmol) while stirring. The disappearance of the yellow color indicates the end of the amidation reaction. The reaction mixture is concentrated and loaded on a flash silica gel column. Elution with 2–6% methanol in methylene chloride allows the isolation of benzyl protected title compound (522 mg, 87%) as a colorless thick oil. $^1$H NMR (250 MHz, $CDCl_3$): δ0.794 (t, 3H, J=7.40), 1.333 (q, 2H, J=7.23), 3.184 (q, 2H, J=7.0), 3.605 (s, 3H),5.383 (s, 2H),6.816 (d, 1H, J=7.24),7.123(d, 1H, J=7.21),7.30–7.92 (s, br, 1H).

(2) 3-Hydroxy-1-methyl-4(1-propylcarbamoyl)-2(1H)-pyridinone (Formula 9C, $R_1$=methyl, R=n-propyl, R'=H)

3-Benzyloxy-1-methyl-4(1-propylcarbamoyl)-2(1H)-pyridinone (301 mg, 1 mmol) and 5% Pd/C catalyst (30 mg) are mixed with ethanol (15 mL), the mixture is stirred under hydrogen (1 atm) at room temperature for three hours. After filtration, the filtrate is rotary evaporated to give a pale pink solid. Crystallization from ethyl acetate gives the titled compound (180 mg, 86%) as a colorless crystalline product, m.p. 163.5°–165° C. $^1$H NMR (250 MHz, DMSO-$d_6$): δ0.883 (t, 3H, J=7.41), 1.524 (q, 2H, J=7.30), 3.234 (q, 2H,J=6.57), 3.469 (s, 3H), 6.524 (d, 1H, J=7.43), 7.185 (d, 1H, J=7.42), 8.467 (s,br, 1H). MS (+FAB,TG/G): 211.1 ($MH^+$, 100%). Anal. for $C_{10}H_{13}N_2O_3$ (209.228), Calcd. (found): C, 57.40 (57.44); H, 6.26 (6.63); N 13.39 (13.25).

Example 4

Preparation of 1,3-bis[(3-hydroxy-1-methyl-2-oxo-1,2-dihydropyridin-4-yl)carboxamido]propane (3-LI-Me-3,2-HOPO, Formula 10, $R_1$=methyl, m=3)

To a solution of 3-hydroxy-4-benzyloxycarbonyl-1-methyl-2(1H)-pyridinone (1.1 g, 4.2 mmol), 2-mercaptothiazoline (0.52 g, 4.4 mmol), and a catalytic amount of DMAP in dry methylene chloride (50 mL), DCC (0.90 g, 4.4 mmol) is added. The resulting yellow mixture is stirred in darkness for four hours, and 1,3-propanediamine (0.15 g, 2 mmol) is added neatly. The mixture is stirred overnight, and filtered to remove any DCU solids, the filtrate is rotary evaporated and loaded onto a flash silica column. Elution with 2–6% methanol in methylene chloride allows the separation of the benzyl-protected precursor (0.98 g) as a pale yellow thick oil. It is dissolved in glacial acetic acid (20 mL) and hydrogenated by using 10% Pd on charcoal as a catalyst. Filtration followed by rotary evaporation gives a pale brown residue which is recrystallized from methanol to give the title compound (555 mg, 73.3%) as a beige powder, m.p. 268°–271° C. (dec). $^1$H NMR (300 MHz, DMSO-$d_6$): δ1.757 (t, 2H), 3.327 (q, 4H), 3.469 (s, 6H), 6.503 (d, 2H, J=7.24), 7.193 (d, 2H, J=7.28), 8.483 (s,br, 2H), 11.7 (s, br, 2H). MS(+FAB, NBA): 377.2 ($MH^+$, 17%), 399.2 ($MNa^+$, 11%). Anal. for $C_{17}H_{20}N_4O_6$ (376.375), Calcd. (found): C, 54.25 (54.17); H, 5.35 (5.49); N, 14.88 (14.59).

Example 5

Preparation of 1,4-bis[(3-hydroxy-1-methyl-2-oxo-1,2-dihydropyridin-4-yl)caboxamido]butane (4-LI-Me-3,2-HOPO, Formula 10, $R_1$=methyl, m=4)

This compound is prepared by the procedure of example 4, except 1,4-butanediamine (160 mg, 1.8 mmol) is used instead of 1,3-propanediamine. Separation and purification of the benzyl-protected precursor are performed as described above, the pure precursor is recrystallized from methanol as a white crystalline solid, m.p. 189°–190° C. It is deprotected by catalytic hydrogenation as described above. The title compound is recrystallized from methanol to give a beige solid product (462 mg, 68.7%), m.p. 265° C. (dec). $^1$H NMR (300 MHz, DMSO-$d_6$): δ1.541 (s, br, 2H), 3.308 (s, br, 4H), 3.463 (s, 6H), 6.515 (d, 2H, J=7.31), 7.187 (d, 2H, J=7.27), 8.483 (t, br, 2H, J=5.34). MS(+FAB, NBA): 391.3 ($MH^+$, 100%), 413.1 ($MNa^+$, 25%). Anal. for $C_{18}H_{22}N_4O_6$. 0.5 $H_2O$ (399.41), Calcd. (found): C, 54.13 (54.67); H, 5.80 (5.91); N, 14.02 (13.58).

Example 6

Preparation of 1,5-bis[(3-hydroxy-1-methyl-2-oxo-1,2-dihydropyridin-4-yl)carboxamido]pentane (5-LI-Me-3,2-HOPO, Formula 10, $R_1$=methyl, m=5)

This compound is prepared by the procedure of example 4, except 1,5-pentanediamine (0.21 g, 2mmol) is used instead of 1,3-propanediamine. Separation and purification of the benzyl-protected precursor are performed as described above, the pure precursor is separated as a pale yellow oil. It is deprotected by catalytic hydrogenation as described above. The deprotected product is recrystallized from methanol to give the title compound (530 mg, 65.7%) as white scale-like micro crystalline product. m.p. 225°–6° C.

(dec). $^1$H NMR (300 MHz, DMSO-d$_6$): δ1.32 (m, 2H), 1.527 (qin, 4H, J=7.17), 3.276 (q, 4H, J=6.49), 3.464 (s, 6H), 6.509 (d, 2H, J=7.33), 7.183 (d, 2H, J=7.34), 8.459 (t, br, 2H, J=5.52). MS (+FAB, NBA): 405 (MH$^+$, 100%), 427.1(MNa$^+$, 25%). Anal. for C$_{19}$H$_{24}$N$_4$O$_6$. 0.56H$_2$O (415.24), Calcd. (found): C, 54.96 (54.89); H, 6.12 (5.99) N, 13.45 (13.27).

Example 7

Preparation of 1,6-bis[(3-hydroxy-1-methyl-2-oxo-1,2-dihydropyridin-4-yl)carboxamido]hexane (6-LI-Me-3,2-HOPO, Formula 10, R$_1$=methyl, m=6)

This compound is prepared by the procedure of example 4, except 1,6-hexanediamine (220 rag, 1.9 mmol) is used instead of 1,3-propanediamine. Separation and purification of the benzyl-protected precursor are performed as described above, the pure precursor is recrystallized from methanol as a white crystalline solid, m.p. 179°–180° C. It is deprotected by catalytic hydrogenation as described above. The title compound is recrystallized from methanol to give a white solid product (530 rag, 73.3%), m.p. 240°–1° C. (dec). $^1$H NMR (300 MHz, DMSO-d$_6$): δ1.32 (s,br, 4H), 1.501 (t, br, 4H, J=6.62), 3.258 (q, 4H, J=6.55), 3.452 (s, 6H), 6.502 (d, 2H, J=7.22), 7.183 (d, 2H, J=7.34), 8.455 (t, br, 2H, J=5.36), 11.8(s, br). MS(+FAB, NBA): 419.2(MH$^+$, 10%), 441.2(MNa$^+$, 29%), 463.2(M +Na$^+$-H$^+$, 15%). Anal. for C$_{20}$H$_{26}$N$_4$O$_6$. 0.25 H$_2$O (422.96), Calcd. (found): C, 56.79 (57.03);H, 6.31 (6.41));N, 13.24 (12.95).

Example 8

Preparation of 1,5-bis[(3-hydroxy-1-methyl-2-oxo-1,2-dihydropyridin-4-yl)carboxamido]-3-oxypentane (5-LI-O-Me-3,2-HOPO, Formula 11, X=O, m=n=2)

This compound is prepared by the procedure of example 4, except 2,2'-oxybis(ethylamine) dihydrochloride (0.25 g, 1.4 retool) is used instead of 1,3-propanediamine. Separation and purification of the benzyl-protected precursor are performed as described above, the pure precursor is separated as a pale yellow oil. It is deprotected by catalytic hydrogenation as described above. The title compound is recrystallized from methanol to give a white solid product (510 mg, 89%), m.p. 205° C. (dec). $^1$H NMR (300 MHz, DMSO-d$_6$): δ3.327 (t, 4H), 3.404 (s, 6H), 3.488 (t, 4H, J=5.32), 6.452 (d, 2H, J=7.33), 7.107 (d, 2H, J=7.31), 8.483 (s,br, 2H). MS(+FAB, NBA): 407.2 (MH$^+$, 100%), 429.2 (MNa$^+$, 72%). Anal. for C$_{18}$H$_{22}$N$_4$O$_7$ (408.20), Calcd. (found): C, 53.19 (53.01); H, 5.48 (5.50); N, 13.72 (13.62).

Example 9

Preparation of N,N,N,-tris[(3-benzyloxy-1-methyl-2-oxo-1, 2-dihydropyridin-4-yl)carboxamidoethyl]-amine (TREN-Me-3,2-HOPO, Formula 12, m=1)

To a solution of 3-benzyloxy-1-methyl-4-(2-thioxothiazolidin-1-yl)carbonyl-2(1H) pyridinone (Formula 24, 1.44 g, 4 mmol) in methylene chloride (50 mL), freshly distilled tris(2-aminoethyl)amine (TREN) (0.18 g, 1.2 mmol) is added, the mixture is stirred overnight and then rotary evaporated and loaded onto a flash silica column. Elution with 2-7% methanol in methylene chloride allows for isolation of the pure benzyl-protected precursor as a pale yellow oil. It is dissolved in glacial acetic acid (10 mL) and hydrogenated by using 10% Pd on charcoal as catalyst. Filtration followed by rotary evaporation gives a pale brown residue which is recrystallized from water to give the title compound (486 mg, 67.1%) as a pale yellow crystalline solid, m.p. 130°–2° C. (dec). 1H NMR (250 MHz, DMSO-d$_6$): δ2.296 (t, 6H, J=5.97), 3.072 (q, 6H, J=5.82), 3.449 (s, 9H, NCH$_3$), 6.458 (d, 3H, J=7.24), 7.122 (d, 3H, J=7.27), 8.46 (t, br, 3H, J=5.3). $^1$H NMR (250 MHz, D$_2$O-NaOD): δ2.901 (t, 6H, J=6.26), 3.450 (s, 9H), 3.520 (t, 6H, J=6.24), 6.568 (d, 3H, J=7.29), 6.609 (d, 3H, J=7.21). MS (+FAB, NBA): 600.3 (MH$^+$). Anal for C$_{27}$H$_{33}$N$_7$O$_9$. 1.5 H$_2$O (626.634) Calcd.(found): C, 51.75 (51.84)); H 5.79 (5.54); N 15.64 (15.59).

Example 10

Preparation of N,N,N,-tris[(3-benzyloxy-1-methyl-2-oxo-1, 2- dihydropyridin-4-yl)carboxamidopropyl]-amine (TRPN-Me-3,2-HOPO, Formula 12, m=2)

This compound is prepared by the procedure of TREN-Me-3,2-HOPO, except tris(3-aminopropyl)amine (TRPN) (0.16 g, 1,1 mmol) is used instead of TREN. Separation and purification of the benzyl-protected precursor are performed as described in example 9. The title compound (392 mg, 56.6%) is obtained by catalytic hydrogenation deprotection followed by precipitation from methanol/ether mixture and collected by filtration as a pale, greenish-yellow solid., m.p. 165° C. (dec) $^1$H NMR (250 MHz, DMSO-d$_6$): δ1,710 (s, br 6H), 2.660 (s,br, 6H), 3.302 (s,br, 6H), 3.429(s, 9H), 6.485 (d, 3H, J=7.30), 7.065 (d, 3H, J=7.30), 8.80 (s br, 3H). $^1$H NMR (250 MHz, D$_2$O-NaOD): δ1,756 (s, br 6H), 2.592 (s,br, 6H), 2.592 (s,br, 6H), 3.330 (s,br, 6H), 3.374 (s, 9H), 6.516 (d, 3H, J=7.27), 6.617 (d, 3H, J=7.17). MS (+FAB, TG/G): 642.2 (MH$^+$, 85%). Anal. for C$_{30}$H$_{39}$N$_7$O$_9$.H$_2$O (659.707), Calcd.(found): C, 54.62 (54.40); H, 6.26 (6.27); N, 14.86 (14.82).

Example 11

Preparation of N,N ,N,-tris[(3-hydroxy-1-methyl-2-oxo-1,2-dihydropyridin-4-yl)carboxamidoethyl]-amine (ME-Me-3, 2-HOPO, Formula 13)

To a solution of 3-benzyloxy-1-methyl-4-(2-thioxothiazolidin-1-yl)carbonyl-2(1H)-pyridinone (Formula 24, 400 mg, 1.1 mmol) in methanol (10 mL), a solution of mesitylenetriamine trihydrochloride (82 mg, 0.3 mmol) in pyridine/water (4:1, 10 mL) is added, the mixture is stirred overnight and rotary evaporated to dryness. The residue is dissolved in methylene chloride and loaded onto a flash silica column. Elution with 2–8% methanol in methylene chloride allows for isolation of the pure benzyl-protected precursor as a pale yellow oil, which solidifies upon standing. The title compound (118 mg, 58.3%) is obtained by catalytic hydrogenation deprotection of the precursor followed by recrystallization from methanol as a white solid, m.p. 168°–70° C. (dec). $^1$H NMR (300 MHz, DMSO-d$_6$): δ3.470(s, 9H),4.463 (d, 6H, J=5.54), 6,495 (d, 3H, J=7.26), 7.147 (s, 3H), 7.159 (d, 3H, J=7.64), 8.913 (t, 3H, J=5.75). MS(+FAB, NBA):619.2(MH$^+$, 100%), 641.2 (MNa$^+$, 20%). Anal. for C$_{30}$H$_{30}$N$_6$O$_9$.1.9 H$_2$O (652.84), Calcd.(found): C, 55.19 (55.31); H, 5.19(5.19); N, 12.87 (12.62).

Example 12

Preparation of N,N,N',N'-tetrakis[(3-hydroxy-1-methyl-2-oxo-1,2-dihydropyridin-4-yl)carboxamido-ethyl]-ethylenediamine (H(2,2)-Me-3,2-HOPO, Formula 14, m=n=2)

To a solution of 3-benzyloxy-1-methyl-4-(2-thioxothiazolidin-1-yl)carbonyl-2(1H)-pyridinone (Formula 24, 1.44 g, 4 mmol) in methylene chloride (50 mL), N,N,N',N'-tetrakis(2-aminoethyl)ethylenediamine (PENTEN) (258 mg, 0.9 mmol) is added. After stirring for tour hours, the mixture is filtered and evaporated to dryness. The residue is loaded onto a flash silica column. Elation with 3–8% methanol in methylene chloride allows for isolation of the pure benzyl-protected precursor as a pale yellow oil. It is dissolved in glacial acetic acid (20 mL), 20% Pd(OH)$_2$ on charcoal catalyst is added and the mixture is hydrogenated under 400 psi at room temperature overnight. Filtration followed by rotary evaporation gives a pale brown residue which is recrystallized from methanol to give the title compound (397 mg, 52.9%) as a white powder, m.p. 270° C. (dec). $^1$H NMR (250 MHz, DMSO-d$_6$): δ2.663 (s,br, 12H), 3.35 (m,br, 8H), 3.436 (s, 12H), 6.465 (d, 4H, J=7.26), 7.093 (d, 4H, J=7.35H), 8.5 (s, br, 4H). MS (+FAB, NBA): 837.3 (MH$^+$, 100%). Anal. for C$_{38}$H$_{48}$N$_{10}$O$_{12}$.H$_2$O (854.884), Calcd.(found): C, 53.39 (53.29); H, 5.89 (5.71): N 16.38 (16.10).

Example 13

Preparation of N,N,N',N'-tetrakis[(3-hydroxy-1-methyl-2-oxo-1,2-dihydropyridin-4-yl)carboxamido-ethyl]-propylenediamine (H(3,2)-N-Me-3,2-HOPO, Formula 14, m=3, n=2)

This compound is prepared by the procedure of H(2,2)-Me-3,2-HOPO, except N,N,N',N'-tetrakis(2-aminoethyl)-propylenediamine (H(3,2)-amine) (76 mg, 0.25 mmol) is used instead of PENTEN. Separation and purification of the benzyl-protected precursor are performed as described in example 12. The title compound (110 mg, 51.5%) is obtained by catalytic hydrogenation deprotection of the precursor followed by recrystallization from methanol as a greenish pale yellow solid, m.p. 141° C. (dec). 1H NMR (300 MHz, DMSO-d$_6$): δ1.639 (s,br, 2H), 2.644 (s,br, 4H), 2.724 (s, br, 8H), 3.400 (s, br, 8H), 3.422 (s, 12H), 6.448 (d, 4H, J=7.19), 7.040 (d, 4H, J=7.23), 8.778 (s,br, 4H). MS(+ FAB, NBA): 851.3 (MH$^+$, 45%). Anal. for C$_{39}$H$_{50}$N$_{10}$O$_{12}$.1.2H$_2$O (875.52), Calcd.(found): C, 53.69 (53.70); H, 6.05 (5.98); N, 16.05 (16.09).

Example 14

Preparation of N,N,N',N'-tetrakis[(3-hydroxy-1-methyl-2-oxo-1,2-dihydropyridin-4-yl)carboxamido-ethyl]-butylenediamine (H(4,2)-Me-3,2-HOPO, Formula 14, m=4, n=2)

This compound is prepared by the procedure of H(2,2)-Me-3,2-HOPO, except N,N,N',N'-tetrakis(2-aminoethyl)-butylenediamine (H(4,2)-amine) (80 mg, 0.25 mmol) is used instead of PENTEN. Separation and purification of the benzyl-protected precursor are performed as described in example 12. The title compound (125 mg, 58.3%) is obtained by catalytic hydrogenation deprotection followed by recrystallization from methanol as a pale yellow solid, m.p. 124° C. (dec). $^1$H NMR (300 MHz, DMSO-d$_6$): δ1.656 (s, br, 2H), 2.719 (s, br, 4H), 2.844 (s,br, 8H), 3.411 (s, br, 8H), 3.450 (s, 12H), 6.403 (d, 4H, J=7.19), 6.969 (d, 4H, J=7.32), 8.811 (s, br, 4H). MS (+FAB, NBA): 865.4 (MH$^+$, 66%). Anal. for C$_{40}$H$_{52}$N$_{10}$O$_{12}$.2.2H$_2$O (904.56), Calcd. (found):C, 53.06(53.11); H, 6.28(6.28); N, 15,47 (15.48).

Example 15

Preparation of DFO-1-Me-3,2-HOPO (Formula 17)
(1) Fe(III)-Bn-DFO-1-Me-3,2-HOPO Complex The mesylate salt of DFO (Desfera, 2.63 g, 4 mmol) and FeCl$_3$.6 H$_2$O (1.08 g, 4 mmol) are dissolved in methanol (120 mL) in a 250 mL round flask. To this purple-red solution, KOH solution (1.018N KOH in methanol (Aldrich), 11.7 mL) is added slowly, while stirring. To the above red Fe(III)-DFO complex (free an-line species) solution, a solution of 3-benzyloxy-1-methyl-4-(2-thioxothiazolidin-1-yl)carbonyl-2(1H)-pyridinone (Formula 24, 1.44 g, 4 mmol) in methanol (50 mE) is added slowly, while stirring and the mixture is then stirred overnight. TLC on silica reveals the formation of benzyl protected Fe(III)-1-Me-3,2-HOPO-DFO complex. The red mixture is evaporated to dryness, then loaded on a flash silica column and gradient eluted with 4–20% methanol in methylene chloride. The main red traction which shows only one spot on TLC (silica) plate is collected and evaporated to dryness, yielding 2.73 g (3.08 mmol, 77.2% based on DFO) of Fe(III)-Bn-DFO-1-Me-3,2-HOPO Complex. Anal for C$_{39}$H$_{56}$N$_7$O$_{11}$Fe. 2H$_2$O (890.805), Calcd.(found): C, 52.58 (52.99);H, 6.79 (7.25);N, 11.00 (11.19);Fe, 6.26 (5.97).

(2) Bn-DFO-1-Me-3,2-HOPO

The above Fe(III)-Bn-DFO-1-Me-3,2-HOPO Complex (2.56 g, 3.0 mmol) is dissolved in a minimum amount of water and the pH is adjusted to above 13 with a 12M NaOH solution. The turbid solution is then filtered to remove the brown Fe(OH)$_3$ precipitate. The slight yellow filtrate is acidified with 6M HCl, at which point the protected DFO-Me-3,2-HOPO separates as very thick pale yellow oily material. After cooling, the oily product is solidified, it is triturated with the mother liquor and then filtered. The title compound (1.24 g, 51.7%) is obtained after washing with cold water, methanol and drying as a white solid product, m.p. 110°–2° C. $^1$H NMR (300 MHz, DMSO-d$_6$): δ1.2–1.5 (m, 18H), 1.967 (s, 3H), 2.276 (t, J=7.04, 4H), 2.586 (t, J=6.83, 4H), 3.007 (q, J=6.14, 2H), 3.456 (t, J=6.94, 6H), 5.203 (s, 2H), 6.262 (d, 1H, J=7.02), 7.3–7.5 (m, 5H), 7.528 (d, 1H, J=7.03), 7.807 (t, br, 2H, J=5.04), 8.220 (t, br, J=5.41), 9.6 (s, br, 3H). MS (+FAB, NBA): m/e 802.4 (MH$^+$, 100%). Anal. for C$_{39}$H$_{59}$N$_7$O$_{11}$.H$_2$O (819.966), Calcd. (found): C, 57.13 (57.37); H, 7.50(7.64); N, 11.96 (11.78).

(3) DFO-Me-3,2-HOPO (Formula 17)

Bn-DFO-Me-3,2-HOPO (0.82 g, 1 mmol) is suspended in methylene chloride (20 mL) in a schlenk flask with a teflon stopcock. Under a flow of argon, the suspension is cooled to 0° C. before boron tribromide (1.9 mL, 20 mmol) is injected. The yellow slurry is stirred at room temperature for 72 hours before pumping off the excess BBr$_3$ and CH$_2$Cl$_2$. The remaining pale yellow solid is suspended in cold water. The raw product is collected by filtration, and then dissolved in a 1M NaOH solution. The solution is then acidified to pH 3 and the resultant precipitate is filtered off and dried to give the title compound (0.37 g, 53%) as a white solid, m.p. 166°–8° C. (dec). $^1$H NMR (300 MHz, DMSO-d$_6$) δ1.20–1.52 (m, 18H), 1.962 (s, 3H), 2.261 (t, 4H, J=7.18), 2.571 (t, 4H, J=7.14), 2.993 (q, 4H, J=6.32), 3.251 (q, 2H, J=6.48), 3.450 (t, 6H, J=7.34),3.458 (s, 3H),6.514 (d, 1H, J=7.24), 7.182 (d, 1H, J=7.30),7.778 (t, br, 2H, J=5.17),8, 484 (t, br, 1H, J=5.02),9.617 (s, 2H), 9.660 (s, 1H). MS (+FAB, NBA): 712.4 (MH$^+$, 85%), 734.4 (MNa$^+$, 82%), 696.4 (60%). Anal for C$_{32}$H$_{53}$N$_7$O$_{11}$ (711.824), Calcd. (found): 53.99 (54.19),7.50 (7.53), 13.77 (13.48).

Example 16

Preparation of TREN-bis-Me-3,2-HOPO-bis-acetic acid (Formula 15)

(1) N,N-Bis[(3-benzyloxy-1-methyl-2-oxo-1,2-dihydropyridin-4-yl)carboxamido-ethyl-N-(2-aminoethyl) amine (Bn-TREN-Bis-Me-3,2-HOPO, Formula 16, Z=CH$_2$CH$_2$NH$_2$)

To a solution of 3-benzyloxy-1-methyl-4-(2-thioxothiazolidin-1-yl)carbonyl-2(1H)-pyridinone (Formula 24, 3.2 g, 8.8 mmol) in CH$_2$Cl$_2$ (150 mL), a solution of TREN (0.63 g, 4.4 mmol) in 150 mL CH$_2$Cl$_2$ is added drop by drop over 16 hours. The reaction mixture is concentrated, loaded on a 11ash silica gel column (φ40×80 mm), and eluted with 4% methanol in methylene chloride to separate 2-mercaptothiazoline and other byproducts. The title compound remains on the top of the column and is separated by further gradient elution with 4–6% $CH_3OH+0.4\%$ Triethylamine. The appropriate fractions are collected and evaporated to give 1.98 g (71%) of a white solid. This is a very useful intermediate to synthesize various mixed 3,2-HOPO chelating agents. $^1H$ NMR (300 MHz, CDCl3): δ2.347 (m, 6H), 2.484 (m, 2H), 3.198 (q, 4H, J=5.97), 3.591 (s, 6H), 5.324 (s, 4H), 6.714 (d, 4H, J=7.20),7,117 (d, 4H, J=7.20), 7.27–7.43(m, 10H), 7.978 (s br, 2H).

(2) Ethylenediamine-N,N-bis[(3-hydroxy-1-methyl-2-oxo-1,2-dihydropyridin-4-yl)carboxamidoethyl]-N',N'-diacetic acid) (TREN-bis-Me-3,2-HOPO-bis-acetate, Formula 15)

N,N-Bis [(3-benzyloxy-1-methyl-2-oxo-1,2-dihydropyridin-4-yl )carboxamido-ethyl -N-(2-aminoethyl) amine (2.0 g, 3.2 mmol), benzyl 2-bromoacetate (2.29 g, 10 mmol) and anhydrous $K_2CO_3$ (1.5 g, 10 mmol) are combined in dry THF (50 mL). The stirred mixture is warmed to 60° C. overnight under nitrogen. After cooling to room temperature, the reaction mixture is filtered, the filtrate is rotary evaporated and applied to a flash silica gel column. Elution with 0.5–4.0% $CH_3OH$ in $CH_2Cl_2$ produces a pale yellow thick oil as pure benzyl protected precursor. It is dissolved in glacial acetic acid (20 mL), 20% $Pd(OH)_2$ on charcoal catalyst (200 mg) is added and the mixture hydrogenated under 400 psi at room temperature overnight. Filtration followed by rotary evaporation gives a pale brown residue which is recrystallized from methanol to give the title compound (0.93 g, 53.1%) as a white powder, m.p. 194°–6° C. (dec). $^1H$ NMR (500 MHz, D20): δ3.291 (s,br, 4H), 3.367 (s, 6H), 3.38–3.39 (m,br, 2H), 3.40–3.42 (m,br, 2H), 3.542 (s,br, 4H), 3.791 (s, NH), 6.351 (d, 2H, J=4.35), 6.839 (d, 2H, J=4.34). MS (+FAB, TG/G): 565.2(MH$^+$, 100%), 587.2 (MNa$^+$, 20%). Anal for $C_{24}H_{32}N_6O_{10}\cdot1.2 H_2O$ (582.824), Calcd. (found): C,49.17(49.68); H, 5.91 (6.15); N, 14.33 (13.98).

Example 17

Preparation of Thorium (IV) Complex with 3-Hydroxy-1-methyl-4-(1-propylcarbamoyl)-2(1H)-pyridinone To a solution of 1-Me-3,2-HOPO propylamide (Formula 9B, R=methyl, R=H, 84 mg, 0.40 mmol) in dry acetonitrile (10 mL), a solution of thorium acetylacetonate (63 mg, 0.1 mmol) in acetonitrile (10 mL) is added while stirring. The clear mixture solution turns turbid after a few minutes, it is refluxed overnight under nitrogen. The resultant precipitate is filtered off and dried to give the title compound (66 mg, 88%) as a beige solid, m.p. 216°–8° C. $^1H$ NMR(300MHz, DMSO): δ0.666(t, 12H, J=7.39), 1.158(q, 8H, J=7.17), 2.956 (q, 8H, J=6.47), 3.487 (s, 6H), 6.819(d, 2H, J=7.03), 6.974 (d, 2H, J=7.17), 4H, J=5.57). MS (+FAB, TG/G) 1069.7 (ThL$_4$H$^+$, 50%), 859.3 (ThL$_3^+$, 100%). Anal for ThC$_{40}$H$_{52}$N$_8$O$_{12}$·2.5H$_2$O (1114.43), Calcd.(found): C, 43.11 (43.13); H, 5.15 (4.91); N, 10.05 (9.79).

Example 18

Preparation of Ferric Ion Complex with 1,3-Bis[(3-hydroxy-1-methyl-2-oxo-1,2-dihydropyridin-4-yl)carboxamido]propane To a suspension of 3-LI-Me-3,2-HOPO (Formula 10, m=3,245 mg, 0.65 mmol) in dry methanol (10 mL), 0.65 mL of 1.018 M KOH/methanol (Aldrich) is added to make a clear solution. A solution of ferric acetylacetonate complex (140 mg, 0.4 mmol) in dry methanol (10 mL) is added to the above ligand solution while stirring and results in a deep red color. The solution is evaporated under vacuum to give a black-red powdery solid, which is loaded on a lipophilic sephadex (LH 20) column and eluted with methanol. The deep red band is collected and rotary evaporated to give the title complex (160 mg, 65%) as a powdery red-black solid. MS (+FAB, NBA): 1235.7 (MH$^+$, 100%), shows typical isotope distribution for iron compounds. Anal for Fe$_2$C$_{51}$H$_{54}$N$_{12}$O$_{18}$·H$_2$O (1252.79), Calcd. (found): C, 48.89 (48.66); H, 4.50 (4.71); N, 13.41 (13.23); Fe, 8.91 (8.75).

Example 19

Preparation and Crystal Structure of Ferric Ion Complex with N,N,N,-Tris[(3-hydroxy-1-methyl-2-oxo-1,2-dihydropyridin-4-yl)carboxamidoethyl]-amine (Fe(III-TREN-3,2-HOPO complex)

To a solution of TREN-Me-3,2-HOPO (63 mg, 0.10 mmol) in distilled water (20 mL), a solution of FeCl$_3$ (27 mg, 0.1 mmol) in water (5 mL) is added while stirring. The purple-red mixture solution is neutralized with saturated NaHCO$_3$ solution. The complex deposits upon standing overnight. It is filtered out and dried to give the title complex (62 mg, 95%) as black-red crystals. MS (+FAB, NBA): 653.3 (MH$^+$, 61%), shows an isotopic distribution typical for iron complexes. Anal. for FeC$_{27}$H$_{30}$N$_7$O$_9$·H$_2$O (670.45), Calcd. (found): C, 48.37 (48.36); H, 4.81 (5.01); N, 14.62 (14.38).

Crystals of this compound suitable for x-ray diffraction are prepared by vapor diffusion of ether into its wet DMF solution. Its chemical formula is 2FeC$_{29}$H$_{30}$N$_7$O$_9$· 2H$_2$O·C$_3$H$_7$NO. Its crystal structure is shown in FIG. 1 and the crystallographic data and parameters for this compound are shown in Table 1. The structure reveals extensive delocalization and a strong hydrogen bonding between the amide proton and its adjacent HOPO oxygen donor, as shown in Formula 8.

TABLE 1

| Crystallographic Data and Parameters for 2FeO$_9$N$_7$C$_{27}$H$_{30}$·2H$_2$O·C$_3$H$_7$NO | |
|---|---|
| Formula: | 2FeO$_9$N$_7$C$_{27}$H$_{30}$·2H$_2$O·C$_3$H$_7$NO |
| Formula Weight (amu) | 1487.13 |
| Temperature (°C.) | –116 |
| Crystal System | triclinic |
| Space Group (#) | P$\bar{1}$ (#2) |
| Cell Constants$^a$ | |
| a (Å) | 12.774(3) |
| b (Å) | 12.838(4) |
| c (Å) | 20.740(7) |
| α (°) | 91.33(3) |
| β (°) | 92.92(2) |
| γ (°) | 102.72(3) |
| Z | 4 |
| V(Å$^3$) | 3311(3) |
| Abs. Coeff., μ$_{calc}$ (cm$^{-1}$) | 5.46 |
| d$_{calc}$ | 1.49 |
| F(000) | 1540 |
| Crystal dimensions (mm) | 0.65 × 0.50 × 0.20 mm |
| Radiation | Mo—Kα (γ = 0.71073) |
| Diffractometer | Enraf-Nonius CAD-4 |
| h, k, l range collected | 0 → 13, –13 → +13, –22 → +22 |
| 2θ range | 3°–45° |
| Scan Type | Omega-2Theta |
| Scan speed (θ, °/min.) | 5.49°/min |
| Reflections collected | 8625 |
| Unique reflections: | 8625 |
| Reflections with (F$_o^2$ > 3*σ(F$_o^2$)) | 6168 |
| Number of parameters | 901 |
| Data/parameter ratio | 6.8 |

TABLE 1-continued

| Crystallographic Data and Parameters for $2FeO_9N_7C_{27}H_{30}\cdot 2H_2O\cdot C_3H_7NO$ | |
|---|---|
| Formula: | $2FeO_9N_7C_{27}H_{30}\cdot 2H_2O\cdot C_3H_7NO$ |
| $R = [\Sigma|\Delta F|/\Sigma|F_o|]$ | 0.081 |
| $R_w = [\Sigma w(\Delta F)^2/\Sigma wF_o^2]$ | 0.103 |
| GOF | 2.994 |
| Final Diff. $\rho_{max}^+$ (e⁻/Å³) | +1.3[b] |

[a]Unit cell parameters and their esd's were derived by a least-squares fitting of the setting angles of 24 reflections the range $9.9° \leq 2\theta \leq 13.9°$.
[b]Located near Fe 2.

Example 20

Preparation and Crystal Structure of Gadolinium (III) Ion Complex with N,N,N,-Tris[(3-hydroxy-1methyl-2-oxo-1,2-dihydropyridin-4-yl)carboxamidoethyl]-amine (Gd(III)-TREN-3,2-HOPO complex)

To a solution of TREN-Me-3,2-HOPO (63 mg, 0.10 mmol) in dry methanol (10 mL), a solution of gadolinium nitrate pentahydrate (43 mg, 0.1 mmol) in dry methanol (10 mL) is added while stirring. The clear solution turns turbid after 2 drops of dry pyridine are added. The mixture is refluxed overnight under nitrogen, during which time the complex deposits as a white fluffy precipitate. It is filtered out, rinsed with cold methanol, and dried to give the title complex (66 mg, 88%) as a white solid. MS (+FAB, NBA): 753.3 (MH⁺, 100%), shows an isotopic distribution typical for gadolinium compounds. Anal. for $GdC_{27}H_{30}N_7O_9\cdot 1.4 H_2O$ (779.05), Calcd. (found): C, 41.62 (41.70); H, 4.24 (4.26); N, 12.58 (12.58).

This complex is very stable in aqueous solution with a formation constant log $\beta_{110}$ of 20.3 and a pM value for $Gd^{3+}$ of 19. This is substantially more stable than any of the $Gd^{3+}$ MRI agents in current clinical use.

Figure 2:
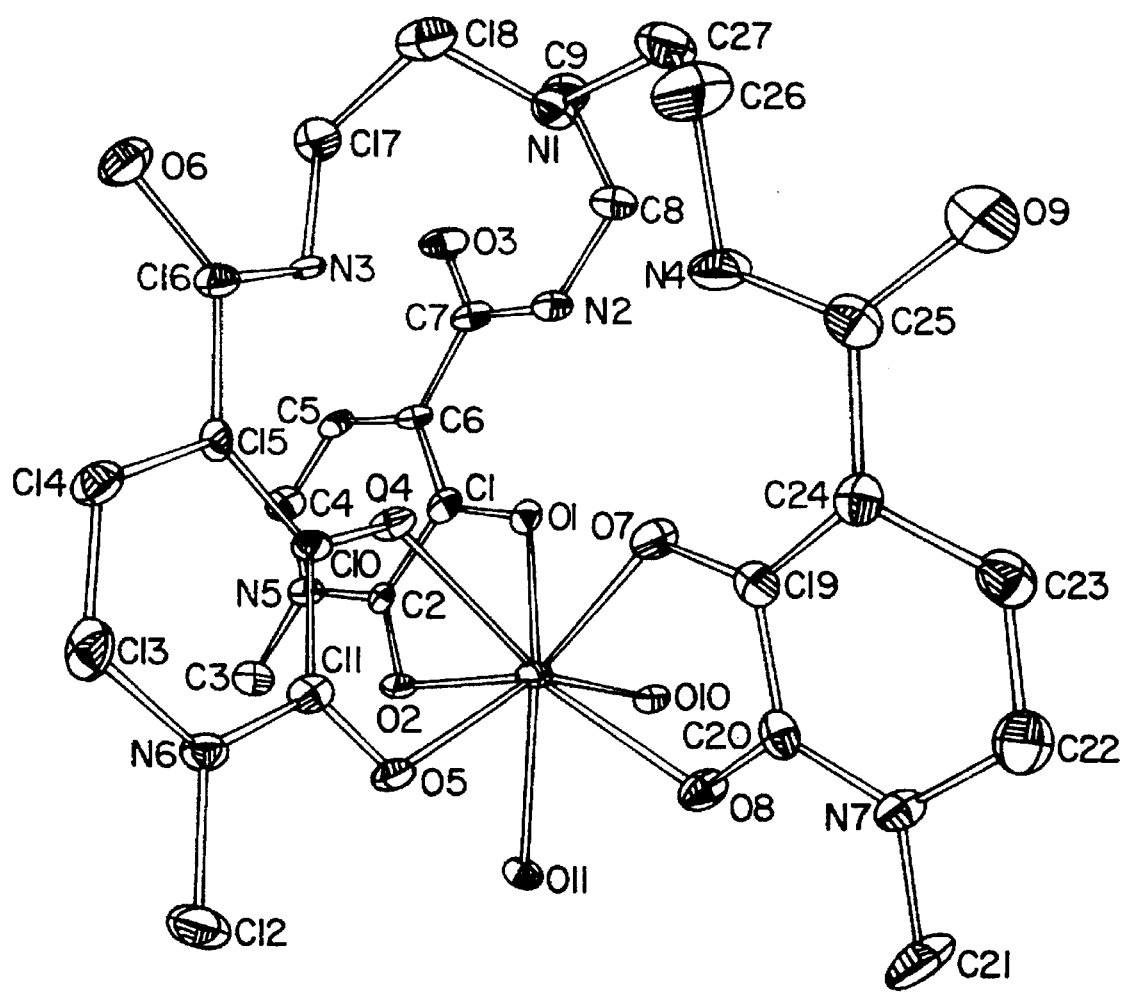
FIG. 2 is a diagram showing the crystal structure of the Gd(III)-TREN-3,2-HOPO complex.

Crystals of this compound suitable for x-ray diffraction are prepared by vapor diffusion of ether into its wet DMF solution. Its chemical formula is $GdC_{29}H_{30}N_7O_9\cdot 2H_2O\cdot C_3H_7NO$. Its crystal structure is shown in FIG. 2 and the crystallographic data and parameters for this compound are shown in Table 2.

Solution of the structure indicates that the compound consists of molecules containing one gadolinium (III) ion which coordinates with a hexadentate TREN-Me-3,2-HOPO ligand and two water molecules, so that the square antiprism coordination requirement of the gadolinium atom is satisfied by the oxygen atoms of three bidentate hydroxypyridonate moieties and two water molecules. The structure reveals extensive delocalization and a strong hydrogen bonding between the amide proton and its adjacent HOPO oxygen donor, as shown in Formula 8. Because of the large number of coordinated water molecules, this class of compounds is expected to show good nuclear magnetic relaxation properties as need for magnetic resonance imaging.

TABLE 2

| Crystallographic Data and Parameters for $GdO_9N_7C_{27}H_{30}\cdot 2H_2O\cdot C_3H_7NO$ | |
|---|---|
| Formula: | $GdO_9N_7C_{27}H_{30}\cdot 2H_2O\cdot C_3H_7NO$ |
| Formula Weight (amu) | 862.96 |
| Temperature (°C.) | −117 |

TABLE 2-continued

| Crystallographic Data and Parameters for $GdO_9N_7C_{27}H_{30}\cdot 2H_2O\cdot C_3H_7NO$ | |
|---|---|
| Formula: | $GdO_9N_7C_{27}H_{30}\cdot 2H_2O\cdot C_3H_7NO$ |
| Crystal System | triclinic |
| Space Group (#) | $P\bar{1}$ (#2) |
| Cell Constants[a] | |
| a (Å) | 10.791(3) |
| b (Å) | 12.901(4) |
| c (Å) | 13.566(4) |
| α (°) | 85.42(2) |
| β (°) | 67.38(2) |
| γ (°) | 74.58(2) |
| Z | 2 |
| V (Å³) | 1680(1) |
| Abs. Coeff., $\mu_{calc}$ (cm⁻¹) | 20.54 |
| $d_{calc}$ | 1.706 |
| F(000) | 874 |
| Crystal dimensions (mm) | 0.30 × 0.11 × 0.08 mm |
| Radiation | Mo—Kα (γ = 0.71073) |
| Diffractometer | Enraf-Nonius CADA |
| h, k, l range collected | 0 → 11, −13 → +13, −14 → +14 |
| 2θ range | 1.5–22.5 |
| Scan Type | Omega-2Theta |
| Scan speed (θ, °/min.) | 5.49°/min |
| Reflections collected | 4377 |
| Unique reflections: | 4377 |
| Reflections with $(F_o^2 > 3*\sigma(F_o^2))$ | 3576 |
| Number of parameters | 460 |
| Data/parameter ratio | 7.8 |
| $R = [\Sigma|\Delta F|/\Sigma|F_o|]$ | 0.036 |
| $R_w = [\Sigma w(\Delta F)^2/\Sigma wF_o^2]$ | 0.039 |
| GOF | 1.385 |
| Final Diff. $\rho_{max}^+$ (e⁻/Å³) | +1.008[b] |

[a]Unit cell parameters and their esd's were derived by a least-squares fitting of the setting angles of 24 reflections the range $23.24° \leq 2\theta \leq 24.56°$.
[b]Located near Gd

Example 21

In Vivo Test of Promoting Excretion of ²³⁸Pu(IV) in Mice by Injected Ligands

The novel chelating agents of the present invention were tested for their effectiveness in promoting excretion of ²³⁸Pu(IV) in n-rice by injected ligands as follows. Mice, in groups of five, each received an intravenous injection of 1850 Bq ²³⁸Pu(IV) in 0.2 mL of citrate buffer. One hour later, 30 µmol/kg of ligand was injected intraperitoneally in 0.5 mL of saline. The mice were killed 24 hours after the Pu injection, frozen, and dissected after partial thawing. The ²³⁸Pu in skeleton, soft tissues, and separated excreta was determined by counting the ²³⁴U L x-rays. Results of removal of ²³⁸Pu(IV) from mice by injected ligands are summarized in Table 3, which also includes data for $CaNa_3$-DTPA and other reference ligands and the Pu-injected controls. As illustrated by the data in Table 3, all the novel 3,2-HOPO chelating agents provide effective Pu removal, and the tetradentate ligands such as 5-LI-O-Me-3,2-HOPO, 5-LI-Me-3,2-HOPO and 4-LI-Me-3,2-HOPO are, surprisingly, as effective or more effective than the hexadentate and octadentate chelating agents. While in the case of multidente 1,2-HOPO and catechoylamide chelating agents, octadentates are always better chelating agents than the correspond hexadentates and tetradentates.

TABLE 3

Removal of $^{238}$Pu(IV) from Mice by Injected Ligands Composed of Me-3,2-HOPO

| | | percent of injected $^{238}$Pu ± SD at 24 h[a,b] | | | | | | |
|---|---|---|---|---|---|---|---|---|
| | no. of mice | tissues | | | | | excreta | |
| Ligand | | skeleton | liver | soft tissue | kidneys | whole body | feces and GI contents | urine 0—24 h |
| Me-3,2-HOPO Ligands[c] | | | | | | | | |
| 5-LI-O-Me-3,2-HOPO | 5 | 11 ± 1.6 | 2.1 ± 0.3[d] | 1.6 ± 0.2[d] | 0.2 | 15 ± 2.1[d] | 61.7 | 23.5 |
| 5-LI-Me-3,2-HOPO | 10 | 10 ± 1.2 | 3.1 ± 0.8[d] | 1.9 ± 0.5 | 0.3 | 16 ± 1.9[d] | 67.6 | 17 |
| 4-LI-Me-3,2-HOPO | 10 | 11 ± 1.7 | 3.7 ± 1.5[d] | 1.9 ± 0.5 | 0.4 | 17 ± 2.4[d] | 63 | 19.4 |
| TREN-Me-3,2-HOPO | 15 | 10 ± 1.1 | 5.0 ± 2.2[d] | 2.5 ± 0.8 | 0.6 | 18 ± 2.7[d] | 43.3 | 37 |
| H(2,2)-Me-3,2-HOPO | 10 | 11 ± 1.7 | 3.8 ± 1.1[d] | 2.8 ± 1.6 | 1.3 | 19 ± 2.9[d] | 45.3 | 36 |
| ME-Me-3,2-HOPO | 5 | 12 ± 1.8 | 6.1 ± 4.9[d] | 3.0 ± 2.0 | 0.9 | 22 ± 8.5[d] | 70.1 | 33.5 |
| 6-LI-Me-3,2-HOPO | 10 | 12 ± 1.8 | 6.5 ± 3.7[d] | 3.7 ± 1.8 | 0.5 | 23 ± 4.9[d] | 62.9 | 14.4 |
| 3-LI-Me-3,2-HOPO | 10 | 14 ± 1.9 | 9.5 ± 4.g[d] | 2.6 ± 0.4 | 0.5 | 27 ± 5.2 | 41.6 | 32 |
| H(3,2)-Me-3,2-HOPO | 5 | 10 ± 2.0 | 14 ± 6.1 | 2.4 ± 0.3[d] | 1.2 | 28 ± 4.8 | 52.1 | 19.5 |
| TREN-bis(Me-3,2-HOPO)-bis acetic acid | 10 | 20 ± 1.7 | 6.6 ± 2.2[d] | 2.7 ± 0.8 | 0.5 | 30 ± 3.6 | 34.6 | 8.7 |
| TRPN-Me-3,2-HOPO | 5 | 14 ± 3.2 | 17 ± 5.0 | 2.0± 1.1 | 0.7 | 33 ± 5.3 | 11.5 | 55 |
| H(4,2)-Me-3,2-HOPO | 5 | 112 ± 2.9 | 29 ± 6.1 | 1.9 ± 1.0 | 1.8 | 46 ± 8.5 | 26.8 | 28 |
| DFO-Me-3,2-HOPO[e] | 10 | 17 ± 2.4 | 13 ± 3.5 | 19 ± 3.0 | 3.0 | 53 ± 3.4 | 26.4 | 21 |
| Reference Ligands[c,e] | | | | | | | | |
| DFO-(1,2-HOPO) | 5 | 6.0 ± 0.5[d] | 5.1 ± 2.2[d] | 2.3 ± 0.5[d] | 0.1 | 13 ± 2.9[d] | 46.7 | 9.5 |
| 3,4,3-LI(1,2-HOPO) | 5 | 7.5 ± 0.7[d] | 8.9 ± 1.7[d] | 1.6 ± 0.6[d] | 0.2 | 18 ± 1.7[d] | 57 | 23 |
| CaNa$_3$-DTPA | 15 | 12 ± 2.3 | 17 ± 4.0 | 3.5 ± 1.6 | 1.1 | 33 ± 6.6 | 5.1 | 61 |
| 3,4-LI(1,2-HOPO) | 5 | 9.9 ± 3.6 | 18 ± 4.8 | 5.8 ± 1.3 | 0.6 | 34 ± 9.2 | 58 | 7.9 |
| 3-LI(1,2-HOPO) | 5 | 17 ± 2.8 | 8.7 ± 1.2[d] | 11 ± 0.8 | 1.4 | 38 ± 4.4 | 53.3 | 8.7 |
| DFO | 10 | 20 ± 11 | 19 ± 13 | 4.5 ± 1.4 | 1.8 | 45 ± 2.5 | 15.1 | 38 |
| ME-(1,2-HOPO) | 5 | 17 ± 2.5 | 18 ± 6.3[d] | 10 ± 1.8 | 1.8 | 47 ± 9.4 | 43 | 9.6 |
| Pu-Injected Controls (fed) | | | | | | | | |
| kill at 24 h | 143 | 31 ± 7.4 | 50 ± 7.9[d] | 7.8 ± 2.1 | 1.8 | 91 ± 6.0 | 4.4 | 3.8 |

[a]Sd = [Σdev$^2$(n − 1)$^{−1}$]$^{1/2}$. No SD is shown for kidneys or excreta, because samples for five-mouse groups were pooled for radioanalysis. Data for each mouse, expressed as % ID, were normal to 100% material recovery; discrepancies are due to rounding.
[b]Ligands were injected (30 μmol kg$^{-1}$, ip) at 1 h, and mice were killed at 24 h after iv injection of $^{238}$Pu(IV) citrate.
[c]Skeleton, liver, and body Pu of ligand-treated groups are significantly less than 24 h Pu-injected controls (t test, p ≦ 0.01).
[d]Significantly different from mice given CaNa$_3$-DTPA (t test, p ≦ 0.01).
[e]Reported previously and shown here to facilitate comparisons.

Example 22

In Vivo Test of Promoting Excretion of $^{238}$Pu(IV) in Mice by Orally Administered Ligands The novel chelating agents of the present invention were tested for their effectiveness in promoting excretion of $^{238}$Pu(IV) by orally administration to mice as follows. Mice in groups of five, each received an intravenous injection of 1850 Bq $^{238}$Pu(IV) in 0.2 mL of citrate buffer. Three minutes later, 30 mmol/kg of ligand was given by gavage in 0.5 ml of saline. The mice were killed 24 hours after the $^{238}$Pu(IV) injection, frozen, and dissected after partial thawing. The $^{238}$Pu(IV) in skeleton, soft tissues, and separated excreta was determined by counting the $^{234}$U L x-rays. Results of removal of $^{238}$Pu(IV) from mice by orally administered ligands are summarized in Table 4, which also includes data for the reference ligands, and the Pu-injected controls. As illustrated by the data in Table 4, the octadentate and hexadentate chelating agents are superior by oral administration, and the hexadentate ligand TREN-Me-3,2-HOPO is the most effective both (by oral and injection)cases.

TABLE 4

Removal of $^{238}$Pu(IV) from Mice by Orally Administered Ligands Composed of Me-3,2-HOPO

| | | percent of administered $^{238}$Pu ± SD at 24 h[a,b] | | | | | | |
|---|---|---|---|---|---|---|---|---|
| | no. of mice | tissues | | | | whole body[c] | excreta | |
| Ligand | | skeleton | liver | soft tissue | kidneys | | feces and GI contents | urine 0–24 h |
| Me-3,2-HOPO Ligands | | | | | | | | |
| H(2,2)-Me-3,2-HOPO | 15 | 11 ± 4.6 | 7,6 ± 6.5 | 4.0 ± 2.1[c] | 0.4 | 23 ≅ 11 | 37.9 | 39 |
| TREN-Me-3,2-HOPO | 10 | 13 ± 5.5 | 8.5 ± 4.7 | 1.9 ± 1.2[c] | 0.7 | 25 ≅ 12 | 34.1 | 42 |
| H(3,2)-Me-3,2-HOPO | 5 | 14 ± 6.7 | 13 ± 5.9 | 4.1 ± 1.9 | 1.4 | 33 ± 13 | 25.4 | 42 |

TABLE 4-continued

Removal of $^{238}$Pu(IV) from Mice by Orally Administered Ligands Composed of Me-3,2-HOPO

| | | percent of administered $^{238}$Pu ± SD at 24 h[a,b] | | | | | | |
|---|---|---|---|---|---|---|---|---|
| | | tissues | | | | | excreta | |
| Ligand | no. of mice | skeleton | liver | soft tissue | kidneys | whole body[c] | feces and GI contents | urine 0–24 h |
| H(4,2)-Me-3,2-HOPO | 5 | 15 ± 6.2 | 19 ± 4.9 | 1.8 ± 0.8 | 1.3 | 37 ± 10 | 10.1 | 52.4 |
| 5-LI—O—Me-3,2-HOPO | 5 | 23 ± 5.9 | 16 ± 4.4 | 4.0 ± 0.8[c] | 0.8 | 43 ± 10 | 44.7 | 12.5 |
| 5-LI—Me-3,2-HOPO | 5 | 23 ± 11 | 24 ± 5.3 | 4.4 ± 2.0 | 0.8 | 53 ± 17 | 27.1 | 20 |
| 4-LI—Me-3,2-HOPO | 5 | 15 ≡ 6.1 | 34 ± 7.7 | 3.6 ± 1.5 | 0.5 | 54 ± 13 | 13.6 | 32.5 |
| DFO—Me-3,2-HOPO | 10 | 20 ± 7.6 | 22 ± 7.7 | 15 ± 4.0 | 2.4 | 60 ± 11 | 17.3 | 22.4 |
| TRPN—Me-3,2-HOPO | 5 | 28 ± 8.0 | 28 ± 3.1 | 4.3 ± 1.7[c] | 0.7 | 60 ± 11 | 35.5 | 5.4 |
| 3-LI—Me-3,2-HOPO | 10 | 27 ± 7.7[c] | 33 ± 4.4 | 5.0 ± 1.2 | 0.8 | 66 ± 11 | 7.9 | 27 |
| TREN-bis(Me-3,2-HOPO)bis acetic acid | 10 | 28 ± 5.2[c] | 38 ± 2.7[d] | 4.1 ± 0.7 | 0.6 | 71 ± 5.6 | 10.0 | 19.1 |
| 6-LI—Me-3,2-HOPO | 10 | 25 ± 3.1[c] | 44 ± 5.0 | 6.2 ± 1.1 | 1.3 | 76 ± 5.8[c] | 9.8 | 14.2 |
| Me—Me-3,2-HOPO | 5 | 34 ± 24.5 | 40 ± 1.8 | 7.5 ± 1.7 | 1.2 | 82 ± 3.9[c] | 6.7 | 12.4 |
| Reference Ligands[c] | | | | | | | | |
| DFO-(1,2-HOPO) | 5 | 12 ± 2.4 | 11 ± 4.9 | 1.3 ± 0.7 | 0.1 | 24 ± 7.7 | 51.4 | 25.7 |
| 3,4,3-LI(1,2-HOPO) | 5 | 33 ± 5.0 | 22 ± 7.7[d] | 3.9 ± 0.8 | 0.2 | 60 ± 8.2 | 12.3 | 29 |
| CaNa$_3$—DTPA | 5 | 35 ± 2.7 | 45 ± 2.4 | 4.1 ± 0.7 | 1.1 | 85 ± 1.8 | 5.0 | 9.5 |
| Pu-Injected Controls (fed) | | | | | | | | |
| kill at 24 h | 20 | 39 ± 7.2 | 43 ± 6.2[d] | 6.0 ± 1.5 | 1.6 | 90 ± 3.6 | 4.5 | 5.4 |

[a]SD = [Σdev$^2$ (n − 1)$^{−1}$]$^{1/2}$. No SD is shown for kidneys or excreta, because samples for five-mouse groups were pooled for radioanalysis. Data for each mouse, expressed as % ID, were normalized to 100% material recovery; discrepancies are due to rounding.
[b]Ligands were given (30 μmole kg$^{-1}$, by garage) at 3 min, and mice were killed at 24 h after iv injection of $^{238}$Pu(IV) citrate.
[c]Mean is significantly less than that of 24-h fasted Pu controls (t test, p ≦ 0.01)
[d]Mean is significantly less than that of mice avaged CaNa$_3$—DTPA (t test, p ≦ 0.01)

Example 23

In Vivo Test of Promoting Excretion of Am(III), Np(IV), and U(VI) in Mice by Injected TREN-Me-3,2-HOPO One of the novel chelating agents of the present invention, TREN-Me-3,2-HOPO, was also tested for effectiveness in promoting excretion of $^{241}$Am (III), $^{237}$Np (V), and $^{232}$U (VI) by injection into mice, as follows: Mice, in groups of five, each received an intravenous injection of (a) 1100 Bq of $^{241}$Am(III) in 0.2 mL of citrate buffer, (b) 150 Bq of $^{232}$UO$_2$Cl$_2$ plus 3.6 mg $^{235}$UO$_2$Cl$_2$ in 0.2 mL of saline, or (c) 200 Bq of $^{237}$NPO$_2$Cl (7.5 mg of $^{237}$NPO$_2$CL) in 0.2 mL of saline. Three to five minutes later, 30 mmol/kg of TREN-Me-3,2-HOPO was injected intraperitoneally in 0.5 mL of saline. The mice were killed 24 hours alter the actinide injection, frozen, and dissected after partial thawing. The skeleton, soft tissues, and separated excreta were radioanalyzed by counting the $^{241}$Am gamma rays, or the alpha particles emitted by $^{237}$Np or $^{232}$U (and its ingrowing daughters). Removal of those actinides from mice by injected TREN-Me-3,2-HOPO is summarized in Table 5, which also includes data for mice similarly treated with CaNa$_3$-DTPA and for actinide-injected controls. As shown by the data in Table 5, TREN-Me-3,2-HOPO reduced the body content of all three actinides to a significantly greater degree than CaNa$_3$-DTPA. Compared with controls, the Am content of all tissues was greatly reduced, the Np content of the soft tissues was significantly reduced, and more than one-half of the U burden in the kidneys was removed. The structure of Am(III)-TREN-Me-3,2-HOPO is considered to resemble that of the Gd(HI) complexes (see example 20). Complexation of the fraction of Np(V) that is reduced in vivo to Np(IV) is considered to resemble that of Pu(IV). Complexation of U(VI) is considered to take place through binding to UO$_2^{2+}$.

TABLE 5

Removal of $^{241}$Am(III), $^{237}$Np(V), or $^{232,234,235}$U(VI) from Mice by Injected TREN—Me-3,2-HOPO[a]

| | percent of injected actinide ± SD at 24 h[a,b,c] | | | | | | |
|---|---|---|---|---|---|---|---|
| | tissues | | | | | excreta | |
| Ligand | skeleton | liver | soft tissue | kidneys | whole body | feces and GI contents | urine 0–24 h |
| Am(III) | | | | | | | |
| TREN—Me-3,2-HOPO | 8.1 ± 1.6[d] | 1.0 ± 0.6[d,e] | 1.6 ± 0.6[d] | 0.2 | 11 ± 1.4[d,e] | 38 | 51 |
| CaNa$_3$—DTPA | 8.5 ± 0.9[d] | 13 ± 1.5[d] | 1.9 ± 0.3[d] | 0.4 | 24 ± 1.3[d] | 8.0 | 68 |

TABLE 5-continued

Removal of $^{241}$Am(III), $^{237}$Np(V), or $^{232,234,235}$U(VI) from Mice by Injected TREN—Me-3,2-HOPO$^a$

| | percent of injected actinide ± SD at 24 h$^{a,b,c}$ | | | | | | |
|---|---|---|---|---|---|---|---|
| | tissues | | | | | excreta | |
| Ligand | skeleton | liver | soft tissue | kidneys | whole body | feces and GI contents | urine 0–24 h |
| Am controls, kill 24 h | 27 ± 5.3 | 50 ± 5.3 | 5.7 ± 0.7 | 1.2 | 84 ± 3.7 | 2.6 | 14 |
| Np(V) | | | | | | | |
| TREN—Me-3,2-HOPO | 34 ± 4.5 | 3.8 ± 5.7$^{d,e}$ | 3.1 ± 1.1 | 1.0 | 42 ± 11$^{d,e}$ | 17 | 40 |
| CaNa$_3$—DTPA | 40 ± 4.4 | 14 ± 5.7 | 3.5 ± 0.9 | 1.3 | 58 ± 8.0 | 1.5 | 40 |
| Np controls, kill 24 h | 37 ± 5.1 | 1.4 ± 2.3 | 5.8 ± 2.3 | 1.7 | 59 ± 4.1 | 41$^f$ | |
| U(VI) | | | | | | | |
| TREN—Me-3,2-HOPO | 16 ± 2.4 | 0.6 ± 0.3 | 1.6 ± 0.3 | 9.4 ± 6.0$^{d,e}$ | 27 ± 8.5$^{d,e}$ | 2.3 | 70 |
| CaNa$_3$—DTPA | 19 ± 3.0 | 1.0$^c$ | 2.2 ± 0.1 | 17 ± 2.8 | 38 ± 0.7 | 62$^f$ | |
| U controls kill 24 h | 17 ± 2.5 | 1.4$^c$ | 2.8 ± 0.5 | 19 ± 6.9 | 40 ± 7.8 | 60$^f$ | |

$^a$Ligands (30 mmol · kg$^{-1}$) i.p at 3 to 5 min after actinide i.v.; kill at 24 h.
$^b$Groups of five mice except: TREN—Me-3,2-HOPO ip at 3 min after 24 h Am, 10; 24 h Am, Np, or U controls, 10. Results are expressed as percent of injected actinide (ID %) normalized to 100% material recovery, discrepancies are due to rounding.
$^c$Standard deviation, SD = [Σdev$^2$(n − 1)$^{-1}$]$^{1/2}$. Kidneys of Am- and Np-injected mice, livers of some U-injected groups, and all excrets were pooled for each five-mouse group.
$^d$Significantly less actinide than appropriate controls (t test, p ≦ 0.01).
$^e$Significantly improved actinide reduction than for mice given CaNa$_3$—DTPA in same protocol.
$^f$Combined excreta.

Example 24

In Vivo Toxicity Test of Injected Ligands in Mice

The test of acute toxicity of these novel ligands was carried out as follows. Groups of five mice were each given a single i.p. injection of 100 mmol/kg of ligand a day for 10 days or given two i.p. injection of 500 mmol/kg in 8 hours. The ligand was dissolved in 0.5 to 1.0 ml of saline at pH 7 to 8. After a period of observation, the mice were killed, selected tissues were removed and fixed for histopathological examination, and unusual findings at autopsy were recorded. Results of the initial test of toxicity of the ligands tested are summarized in Table 6. The highly effective ligands, such as TREN-Me-3,2-HOPO, 5-LI-Me-3,2-HOPO and 5-LI-O-Me-3,2-HOPO proved to be of low toxicity, even at the relatively high dosage of 2×500 μmol/kg in 8 hours.

TABLE 6

Initial Evaluation of Acute Toxicity in Mice of Ligands Composed of 1-Me-3,2-HOPO$^a$

| | study length | no of | no. of | percent control mean ± SD$^d$ | | |
|---|---|---|---|---|---|---|
| protocol and ligand | (d)$^b$ | mice | survivors$^c$ | body weight | kidney weight | plasma urea N |
| I. 100 μmol · kg$^{-1}$ × 10 daily | | | | | | |
| TREN—Me-3,2-HOPO | 11 | 5 | 5 | 102 ± 1 | — | 112 ± 10 |
| TERN—Me-3,2-HOPO | 21 | 5 | 5 | 106 ± 4 | — | 120 ± 9 |
| H(2,2)-Me-3,2-HOPO | 11 | 5 | 5 | 92 ± 6 | — | 223 ± 28 |
| H(2,2)-Me-3,2-HOPO | 21 | 5 | 5 | 87 ± 9 | — | 225 ± 188 |
| 5-LI—Me-3,2-HOPO | 11 | 5 | 5 | 102 ± 5 | 109 ± 14 | 89 ± 1 |
| 5-LI—Me-3,2-HOPO | 21 | 5 | 5 | 102 ± 5 | 100 ± 4 | 101 ± 2 |
| 5-LI—O—Me-3,2-HOPO | 11 | 5 | 5 | 103 ± 5 | 100 ± 19 | 83 ± 5 |
| 5-LI—O—Me-3,2-HOPO | 21 | 5 | 5 | 101 ± 5 | 111 ± 5 | 86 ± 18 |
| IA. 100 μmol · kg$^{-1}$ × 2 daily | | | | | | |
| 3-LI—Me-3,2-HOPO | 6 | 10 | 0 | 89 ± 4 | 222 ± 29 | >1800 |
| 6-LI—Me-3,2-HOPO | 11 | 5 | 3 | 101 ± 5 | 112 ± 13 | 92 ± 6 |
| IB. 100 μmol · kg$^{-1}$ | | | | | | |
| 4-LI—(Me-3,2-HOPO | 5 | 3 | 0 | 85 ± 8 | 190 ± 63 | >2000 |
| II. 500 μmol · kg$^{-1}$ × 2 in 8 h | | | | | | |
| TREN—(Me-3,2-HOPO | 8 | 19$^e$ | 19 | 101 ± 4 | — | 119 ± 15 |
| H(2,2)-Me-3,2-HOPO) | 8 | 10 | 3 | 94 ± 6 | — | 169 ± 10 |
| 5-LI—Me-3,2-HOPO | 11 | 5 | 5 | 99 ± 3 | 109 ± 9 | 98 ± 18 |
| 5-LI—O—Me-3,2-HOPO | 11 | 10 | 10 | 100 ± 2 | 108 ± 10 | 77 ± 10 |

TABLE 6-continued

Initial Evaluation of Acute Toxicity in Mice of Ligands Composed of 1-Me-3,2-HOPO[a]

| protocol and ligand | study length (d)[b] | no of mice | no. of survivors[e] | percent control mean ± SD[d] | | |
|---|---|---|---|---|---|---|
| | | | | body weight | kidney weight | plasma urea N |

[a]Control data: Body weight ratio, (W(t)/W(o)) 8 to 11d, 1.01 ± 0.03(15); 21d, 1.06 ± 0.06(10). Kidney weight (g), 2 × left kidney, 0.44(25). Plasma urea N (mg dL$^{-1}$)(15 groups of five) range 11.4 ± 1.2 to 22.2 ± 2.5, median 20.2 ± 2.3, grand mean 15 geoups 18.5 ± 3.2.
[b]Days after first ligand injection
[c]Number of survivors and of autopsied mice contributing numerical data, with two exceptions. In the case of 3-LI—Me-3,2-HOPO data are shown for two moribound mice autopsied on d 3; allmice were dead by d3. In all cases mice found dead were not autopsied.
[d]Underlined means significantly different from control means, t test, $p < 0.01$.
[e]Two replicate 10-mouse groups, one mouse lost in an injection accident.

We claim:

1. A chelating agent comprised of a plurality of chelating functional units joined by one or more linking members, said chelating functional units independently selected from the group consisting of

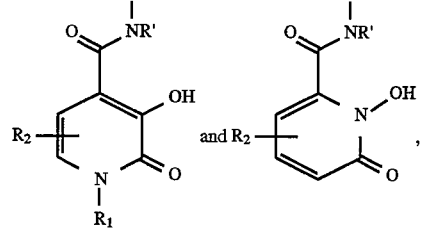

in which at least one of said plurality of chelating functional units on said chelating agent is

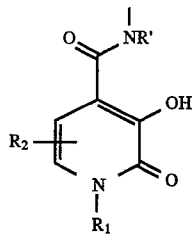

wherein

R$_1$ and R$_2$ are independently selected from the group consisting of hydrogen, C$_1$-aliphatic hydrocarbon groups, and C$_{1-4}$ aliphatic hydrocarbon groups substituted by a single halide, hydroxy, carboxy, acrylamido group or an aryl group, and R' is a member selected from the group consisting of a bond to a linking member, a hydrogen atom, C$_{1-8}$ aliphatic hydrocarbon groups, aryl groups, and C$_{1-8}$ aliphatic hydrocarbon groups substituted by amino, carboxy, or hydroxy groups.

2. A chelating agent in accordance with claim 1, in which R' is a member selected from the group consisting of a hydrogen atom, C$_{1-8}$ aliphatic hydrocarbon groups, aryl groups, and C$_{1-8}$ aliphatic hydrocarbon groups substituted by amino, carboxy, or hydroxy groups.

3. A chelating agent in accordance with claim 1, which is a member selected from the group consisting of

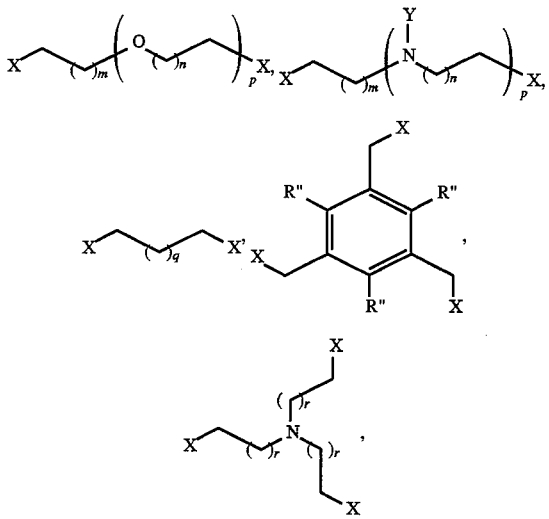

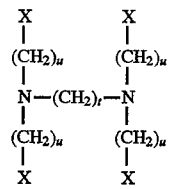

, and

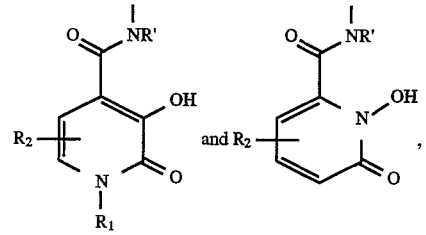

in which:

each X is a chelating functional unit independently selected from the group consisting of with the proviso that at least one of said chelating functional units is

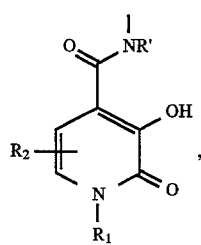

R" is a member selected from the group consisting of H and alkyl,

Y is a member selected from the group consisting of

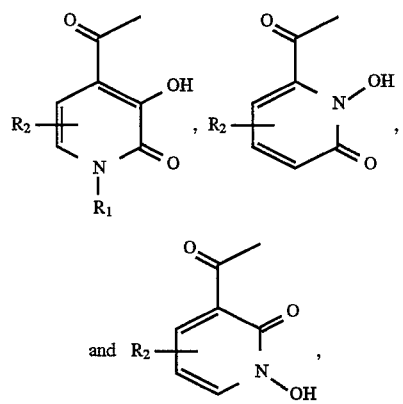

m is 1–3, n is 1–3, p is 1–3, q is 1–6, r is 1 or 2, s is 1 or 2, t is 2–6, and u is 2–4.

4. A chelating agent in accordance with claim 1 further comprising at least one additional chelating functional unit joined to said one or more linking members, said additional chelating functional unit selected from the group consisting of amino acetic acid, catechols, 2,3-dihydroxyterephthalamides, and hydroxamic acids.

5. A chelating agent in accordance with claim 1 in which all chelating functional units are

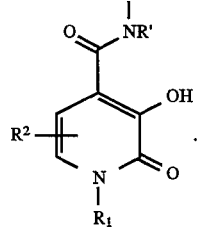

6. A chelating agent in accordance with claim 1 in which said polymeric linking member is a member selected from the group consisting of poly(styrenedivinylbenzene), agarose, and polyacrylamide.

7. The chelating agent

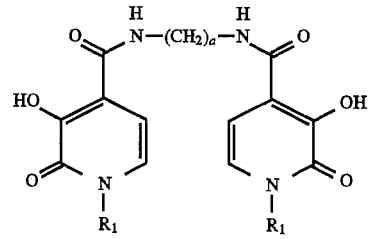

in which:

$R_1$ is a member selected from the group consisting of hydrogen, $C_{1-4}$ aliphatic hydrocarbon groups, and $C_{1-4}$ aliphatic hydrocarbon groups substituted by a single halide, hydroxy, carboxy, or aryl group; and a is 2–9.

8. The chelating agent

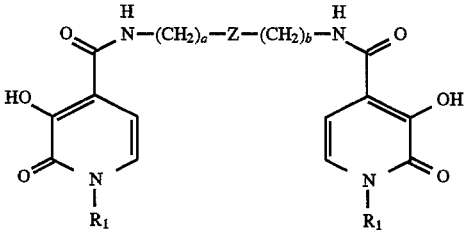

in which:

$R_1$ is a member selected from the group consisting of hydrogen, $C_{1-4}$ aliphatic hydrocarbon groups, and $C_{1-4}$ aliphatic hydrocarbon groups substituted by a single halide, hydroxy, carboxy, or aryl group;

Z is a member selected from the group consisting of O, NH, N—alkyl, and N—aryl;

a is 2–4; and b is 2–4.

9. The chelating agent

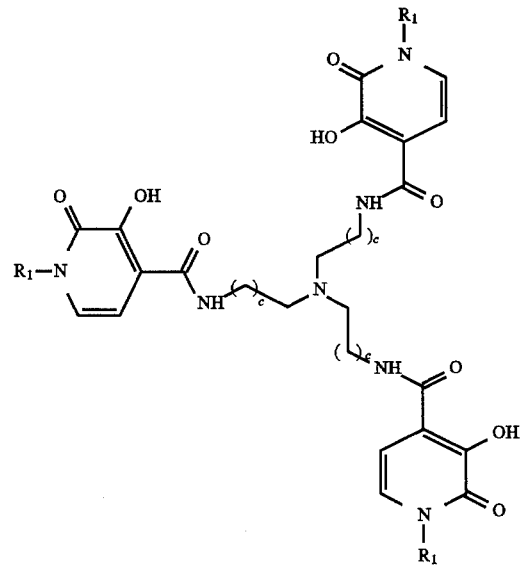

in which:

$R_1$ is a member selected from the group consisting of hydrogen, $C_{1-4}$ aliphatic hydrocarbon groups, and $C_{1-4}$ aliphatic hydrocarbon groups substituted by a single halide, hydroxy, carboxy, or aryl group; and each c is independently 1–3.

10. The chelating agent of claim 9 in which c is 1.

11. The chelating agent

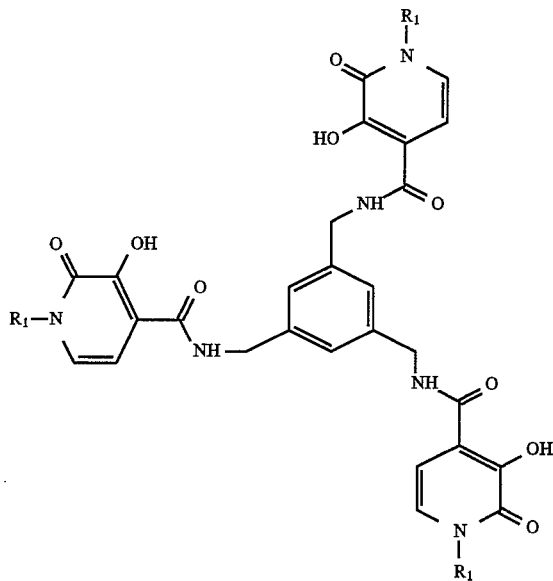

in which $R_1$ is a member selected from the group consisting of hydrogen, $C_{1-4}$ aliphatic hydrocarbon groups, and $C_{1-4}$ aliphatic hydrocarbon groups substituted by a single halide, hydroxy, carboxy, or aryl group.

12. The chelating agent

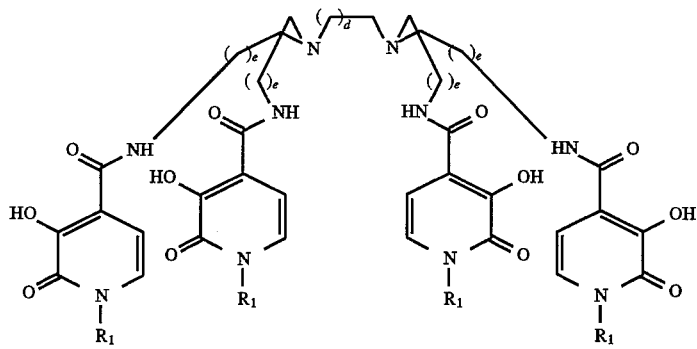

in which:

$R_1$ is a member selected from the group consisting of hydrogen, $C_{1-4}$ aliphatic hydrocarbon groups, and $C_{1-4}$ aliphatic hydrocarbon groups substituted by a single halide, hydroxy, carboxy, or aryl group;

d is 1–4; and each e is independently 1–4.

13. The chelating agent

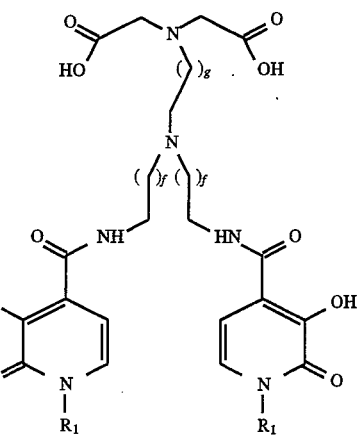

in which:

$R_1$ is a member selected from the group consisting of hydrogen, $C_{1-4}$ aliphatic hydrocarbon groups, and $C_{1-4}$ aliphatic hydrocarbon groups substituted by a single halide, hydroxy, carboxy, or aryl group;

each f is independently 1–4; and g is 1–4.

14. The chelating agent

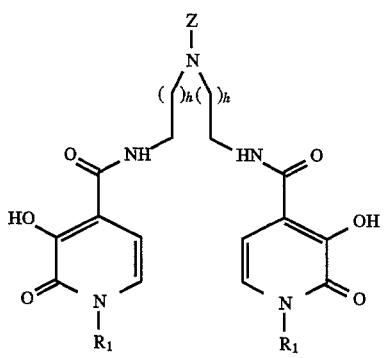

in which:

R₁ is a member selected from the group consisting of hydrogen, $C_{1-4}$ aliphatic hydrocarbon groups, and $C_{1-4}$ aliphatic hydrocarbon groups substituted by a single halide, hydroxy, carboxy, or aryl group;

Z is a member selected from the group consisting of hydrogen, $C_{1-40}$ hydrocarbon groups, 2-hydroxyethyl, 2-aminoethyl, and $C_{1-4}$ aliphatic hydrocarbon groups substituted by a single carboxy, sulpho, acrylamido or aryl group; and each h is independently 1–4.

15. The chelating agent of claim 14 in which Z is $C_{1-40}$ hydrocarbon.

16. The chelating agent

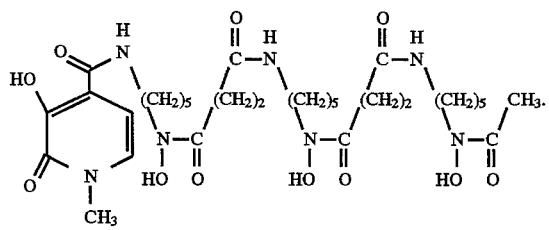

17. The chelating agent

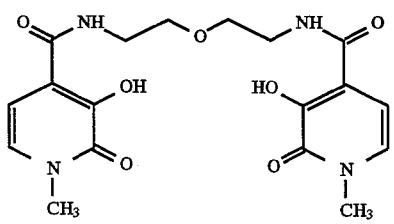

18. The chelating agent

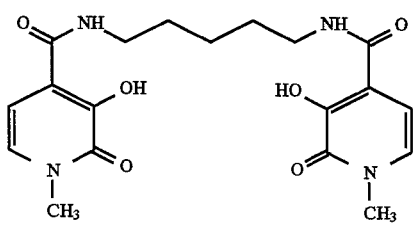

19. The chelating agent

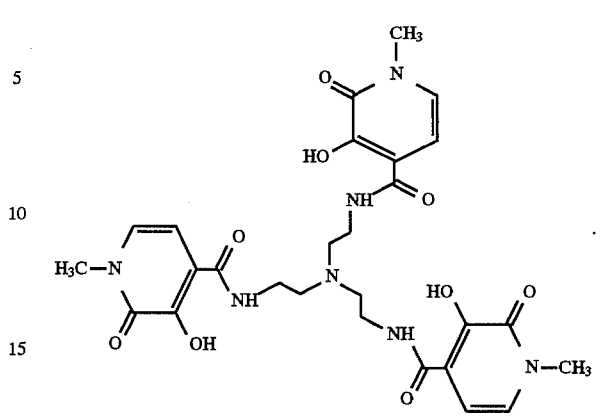

20. The chelating agent

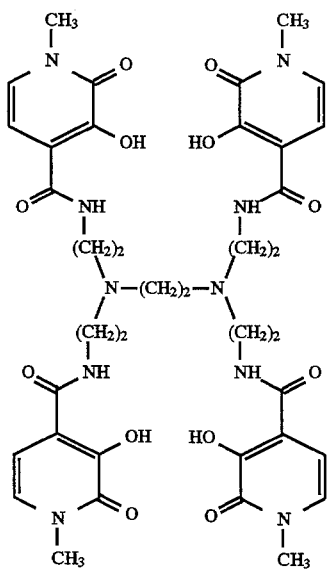

21. A pharmaceutical composition comprising:

(a) a chelating agent comprised of a plurality of chelating functional units joined by one or more linking members, said chelating functional units independently selected from the group consisting of

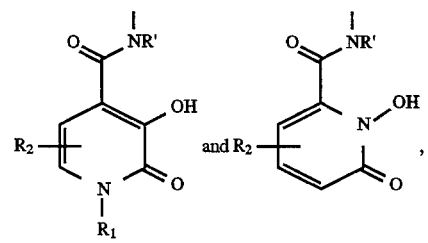

in which at least one of said plurality of chelating functional units on said chelating agent is

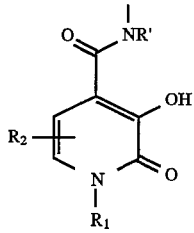

wherein $R_1$ and $R_2$ are independently selected from the group consisting of hydrogen, $C_{1-4}$ aliphatic hydrocarbon groups, and $C_{1-4}$ aliphatic hydrocarbon groups substituted by a single halide, hydroxy, carboxy, acrylamido group or an aryl group, and R' is a member selected from the group consisting of a bond to a linking member, a hydrogen atom, $C_{1-8}$ aliphatic hydrocarbon groups, aryl groups, and $C_{1-8}$ aliphatic hydrocarbon groups substituted by amino, carboxy, or hydroxy groups, and (b) a pharmaceutically acceptable diluent or carrier.

22. A pharmaceutical composition in accordance with claim 21, in which R' is a member selected from the group consisting of a hydrogen atom, $C_{1-8}$ aliphatic hydrocarbon groups, aryl groups, and $C_{1-8}$ aliphatic hydrocarbon groups substituted by amino, carboxy, or hydroxy groups.

23. A pharmaceutical composition in accordance with claim 21 in which said chelating agent is a member selected from the group consisting of

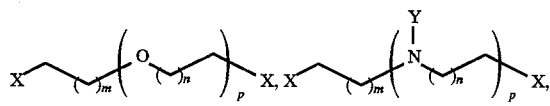

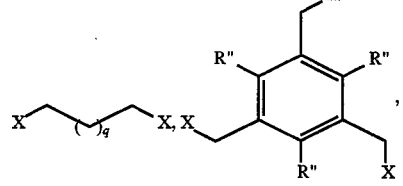

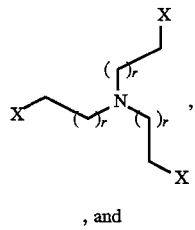

, and

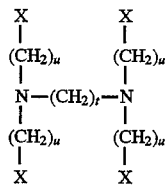

in which:

each X is a chelating functional unit independently selected from the group consisting of

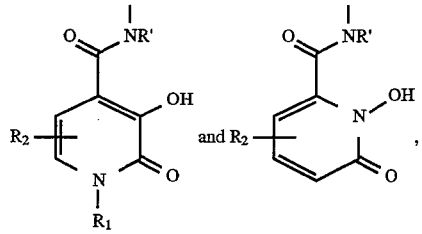

with the proviso that at least one of said chelating functional units is

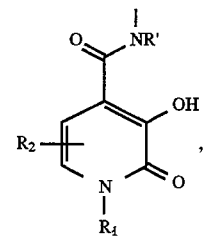

R" is a member selected from the group consisting of H and alkyl,

Y is a member selected from the group consisting of

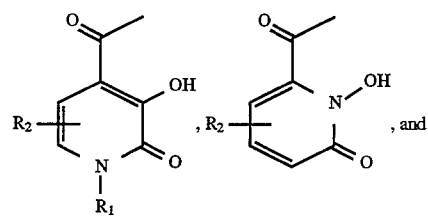

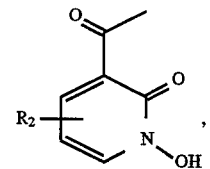

m is 1-3,
n is 1-3,
p is 1-3,
q is 1-6,
each r is independently 1 or 2,
each s is independently 1 or 2,
t is 2-6, and
each u is independently 2-4.

24. A pharmaceutical composition in accordance with claim 21 in which said chelating agent further comprises at least one additional chelating functional unit joined to said one or more linking members, said additional chelating functional unit selected from the group consisting of amino acetic acid, catechols, 2,3-dihydroxyterephthalamides, and hydroxamic acids.

25. A pharmaceutical composition in accordance with claim 21 in which all chelating functional units in said chelating agent are

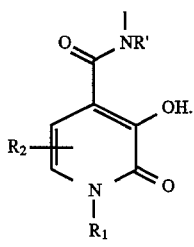

26. A pharmaceutical composition in accordance with claim 21 containing a single linking member, said linking member being a polymeric member.

27. A pharmaceutical composition in accordance with claim 21 in which said polymeric linking member is a member selected from the group consisting of poly(styrene-divinylbenzene), agarose, and polyacrylamide.

28. A pharmaceutical composition comprising an effective amount of the chelating agent

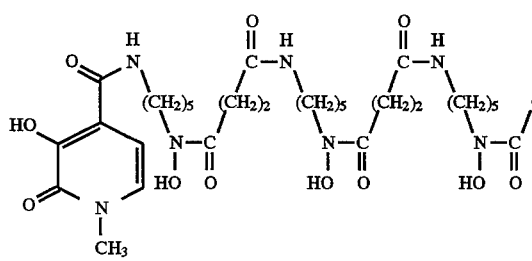

and a pharmaceutically acceptable diluent or carrier.

29. A pharmaceutical composition comprising an effective amount of the chelating agent

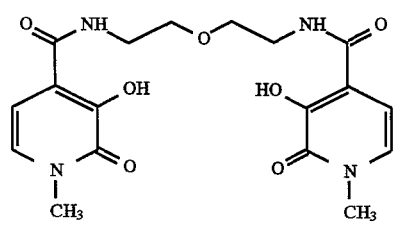

and a pharmaceutically acceptable diluent or carrier.

30. A pharmaceutical composition comprising an effective amount of the chelating agent

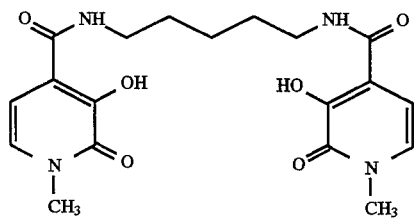

and a pharmaceutically acceptable diluent or carrier.

31. A pharmaceutical composition comprising an effective amount of the chelating agent

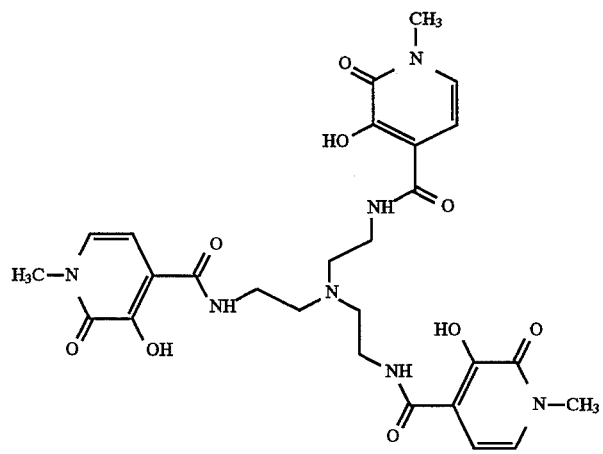

and a pharmaceutically acceptable diluent or carrier.

32. A pharmaceutical composition comprising an effective amount of the chelating agent

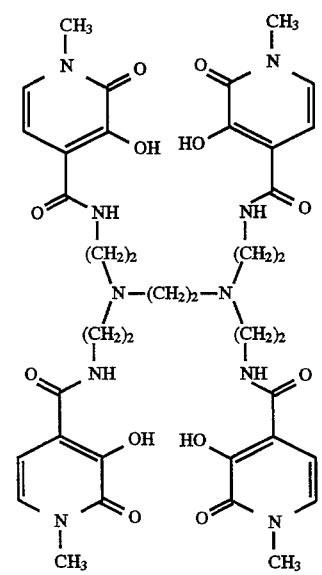

and a pharmaceutically acceptable diluent or carrier.

33. An MRI diagnosis agent containing a complex of a chelating agent comprised of a plurality of chelating functional units joined by one or more linking members, said chelating functional units independently selected from the group consisting of

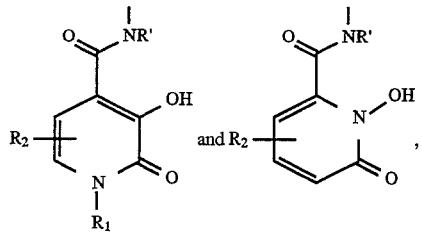

in which at least one of said plurality of chelating functional units on said chelating agent is

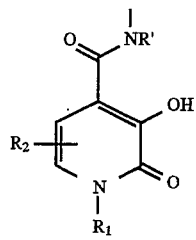

wherein $R_1$ and $R_2$ are independently selected from the group consisting of hydrogen, $C_{1-4}$ aliphatic hydrocarbon groups, and $C_{1-4}$ aliphatic hydrocarbon groups substituted by a single halide, hydroxy, carboxy, acrylamido group or an aryl group, and R' is a member selected from the group consisting of a bond to a linking member, a hydrogen atom, $C_{1-8}$ aliphatic hydrocarbon groups, aryl groups, and $C_{1-8}$ aliphatic hydrocarbon groups substituted by amino, carboxy, or hydroxy groups.

34. An MRI diagnostic agent in accordance with claim 33, in which R' is a member selected from the group consisting of a hydrogen atom, $C_{1-8}$ aliphatic hydrocarbon groups, aryl groups, and $C_{1-8}$ aliphatic hydrocarbon groups substituted by amino, carboxy, or hydroxy groups.

35. An MRI diagnostic agent in accordance with claim 33, in which said chelating agent is a member selected from the group consisting of

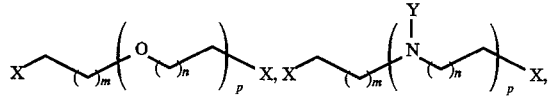

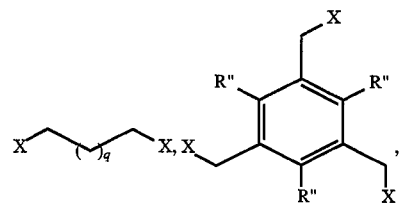

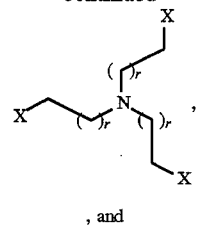

, and

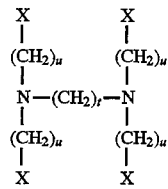

in which:

each X is a chelating functional unit independently selected from the group consisting of

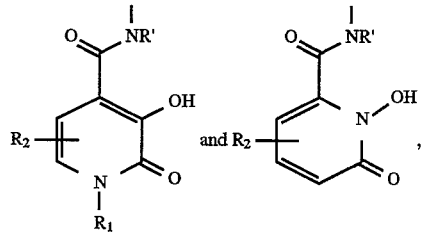

with the proviso that at least one of said chelating functional units is

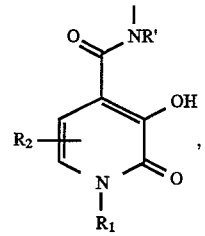

R" is a member selected from the group consisting of H and alkyl,

Y is a member selected from the group consisting of

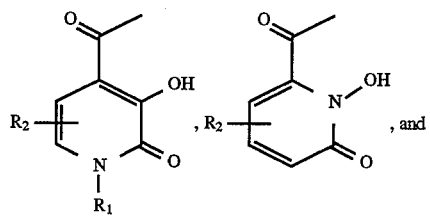

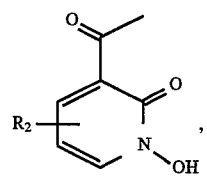

m is 1-3, n is 1-3, p is 1-3, q is 1-6, each r is independently 1 or 2, each s is independently 1 or 2, t is 2-6, and each u is independently 2-4.

36. An MRI diagnostic agent in accordance with claim 33, in which said chelating agent further comprises at least one additional chelating functional unit joined to said one or more linking members, said additional chelating functional unit selected from the group consisting of amino acetic acid, catechols, 2,3-dihydroxyterephthalamides, and hydroxamic acids.

37. An MRI diagnostic agent in accordance with claim 33 in which all chelating functional units of said chelating agent are

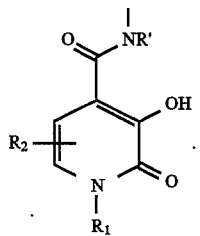

38. An MRI diagnostic agent in accordance with claim 33 in which said polymeric linking member is a member selected from the group consisting of poly (styrenedivinylbenzene), agarose, and polyacrylamide.

39. An MRI diagnostic agent containing the chelating agent

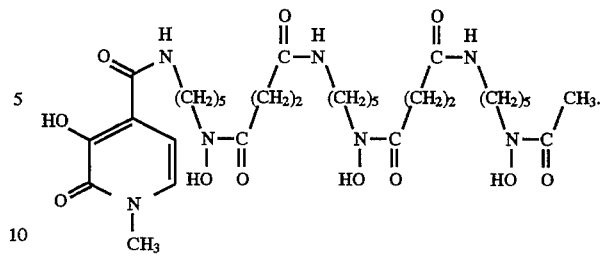

40. An MRI diagnostic agent containing the chelating agent

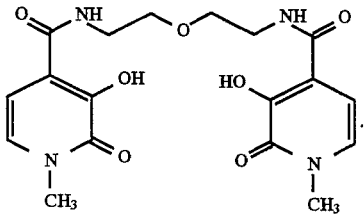

41. An MRI diagnostic agent containing the chelating agent

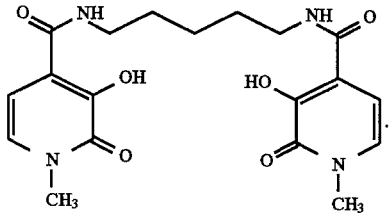

42. An MRI diagnostic agent containing the chelating agent

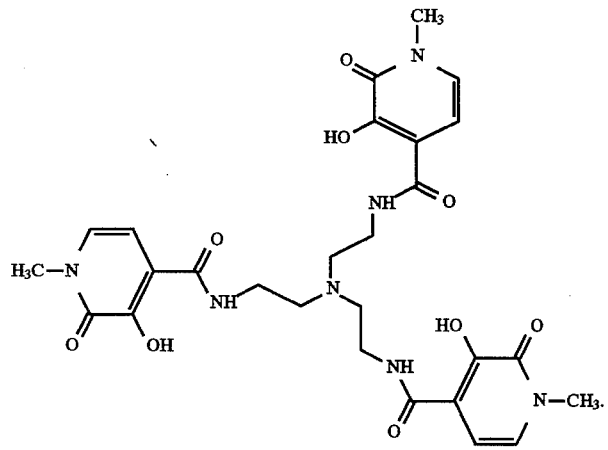

43. An MRI diagnostic agent containing the chelating agent
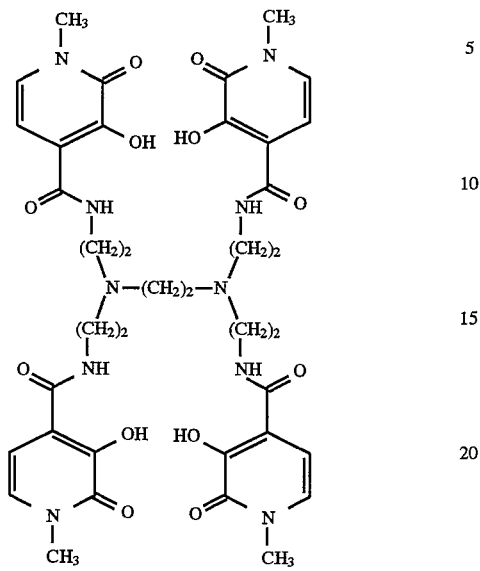
* * * * *